United States Patent
Vaidya et al.

(10) Patent No.: US 11,234,996 B2
(45) Date of Patent: *Feb. 1, 2022

(54) TREATMENT METHODS FOR FIBROSIS TARGETING SMOC2

(71) Applicant: The Brigham and Women's Hospital, Inc., Boston, MA (US)

(72) Inventors: Vishal S. Vaidya, Cambridge, MA (US); Casimiro Gerarduzzi, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/079,002

(22) PCT Filed: Feb. 21, 2017

(86) PCT No.: PCT/US2017/018753
§ 371 (c)(1),
(2) Date: Aug. 22, 2018

(87) PCT Pub. No.: WO2017/147087
PCT Pub. Date: Aug. 31, 2017

(65) Prior Publication Data
US 2019/0282603 A1 Sep. 19, 2019

Related U.S. Application Data

(60) Provisional application No. 62/299,618, filed on Feb. 25, 2016.

(51) Int. Cl.
*C07H 21/04* (2006.01)
*A61K 31/712* (2006.01)
*A61P 13/12* (2006.01)
*C07K 16/28* (2006.01)
*C12N 15/113* (2010.01)
*C07K 16/18* (2006.01)
*A61P 43/00* (2006.01)

(52) U.S. Cl.
CPC ............ *A61K 31/712* (2013.01); *A61P 13/12* (2018.01); *A61P 43/00* (2018.01); *C07K 16/18* (2013.01); *C07K 16/2842* (2013.01); *C12N 15/113* (2013.01); *C07K 2317/76* (2013.01); *C12N 2310/14* (2013.01)

(58) Field of Classification Search
None
See application file for complete search history.

(56) References Cited

FOREIGN PATENT DOCUMENTS

WO WO 2015/138532 9/2015

OTHER PUBLICATIONS

Bornstein and Sage, "Matricellular proteins: extracellular modulators of cell function," Curr Opin Cell Biol, 2002, 14 (5):608-16.
Bradshaw et al., "Pressure overload-induced alterations in fibrillar collagen content and myocardial diastolic function: role of secreted protein acidic and rich in cysteine (SPARC) in post-synthetic procollagen processing," Circulation, 2009, 119 (2):269-80.
Breyer and Susztak, "The next generation of therapeutics for chronic kidney disease," Nat Rev Drug Discov, 2016, 15: 568-588.
Chau et al., "MicroRNA-21 promotes fibrosis of the kidney by silencing metabolic pathways," Sci Transl Med, 2012, 4 (121):121ra18.
Craciun et al., "RNA Sequencing Identifies Novel Translational Biomarkers of Kidney Fibrosis," J Am Soc Nephrol,. 2016, 27 (6):1702-13.
Craciun et al., "Pharmacological and genetic depletion of fibrinogen protects from kidney fibrosis," Am J Physiol Renal Physiol, 2014, 307 (4):F471-84.
Dobin et al., "STAR: ultrafast universal RNA-seq aligner," Bioinformatics, 2013, 29 (1):15-21.
Duffield, "Cellular and molecular mechanisms in kidney fibrosis," J Clin Invest, 2014, 124 (6):2299-306.
Ferenbach and Bonventre, "Mechanisms of maladaptive repair after AKI leading to accelerated kidney ageing and CKD," Nat Rev Nephrol, 2015, 11 (5):264-76.
Garcia-Alcalde et al., "Qualimap: evaluating next-generation sequencing alignment data," Bioinformatics, 2012, 28 (20):2678-9.
Gerarduzzi et al., "Prostaglandin E (2)-dependent blockade of actomyosin and stress fibre formation is mediated through S1379 phosphoiylation of ROCK2," J Cell Biochem, 2014, 115 (9):1516-27.
Greenberg et al., "FAK-dependent regulation of myofibroblast differentiation," FASEB J, 2006, 20 (7):1006-8.
Grgic et al., "The origin of interstitial myofibroblasts in chronic kidney disease," Pediatr Nephrol, 2012, 27 (2):183-93.
Grinnell, "Fibroblast biology in three-dimensional collagen matrices," Trends Cell Biol, 2003, 13 (5):264-9.
Hinz, "It has to be the αv: myofibroblast integrins activate latent TGF-β1," Nat Med, 2013, 19 (12):1567-8.
Humphrey et al., "Mechanotransduction and extracellular matrix homeostasis," Nat Rev Mol Cell Biol, 2014, 15 (12):802-12.
International Preliminary Report on Patentability in International Application No. PCT/US2017/018753, dated Aug. 28, 2018, 8 pages.
International Search Report and Written Opinion in International Application No. PCT/US2017/018753, dated Jul. 31, 2017, 16 pages.
Jendraschak and Sage, "Regulation of angiogenesis by SPARC and angiostatin: implications for tumor cell biology," Semin Cancer Biol, 1996, 7 (3):139-46.
LeBleu et al., "Origin and function of myofibroblasts in kidney fibrosis," Nat Med, 2013, 19 (8):1047-53.
Liao et al., "featureCounts: an efficient general purpose program for assigning sequence reads to genomic features," Bioinformatics, 2014, 30 (7):923-30.

(Continued)

*Primary Examiner* — Kimberly Chong
(74) *Attorney, Agent, or Firm* — Fish & Richardson P.C.

(57) ABSTRACT

Described herein are methods for treating fibrosis, e.g., kidney fibrosis, using agents that target Secreted Modular Calcium-binding protein 2 (SMOC2).

15 Claims, 28 Drawing Sheets
Specification includes a Sequence Listing.

(56) References Cited

OTHER PUBLICATIONS

Liu et al., "The SPARC-related factor SMOC-2 promotes growth factor-induced cyclin D1 expression and DNA synthesis via integrin-linked kinase," Mol Biol Cell, 2008, 19(1):248-61.
Love et al., "Moderated estimation of fold change and dispersion for RNA-seq data with DESeq2," Genome Biol, 2014, 15 (12):550.
Luo et al., "GAGE: generally applicable gene set enrichment for pathway analysis," BMC Bioinformatics, 2009, 10: 161.
Maier et al., "The widely expressed extracellular matrix protein SMOC-2 promotes keratinocyte attachment and migration," Exp Cell Res, 2008, 314 (13):2477-87.
Martin, "Cutadapt removes adapter sequences from high-throughput sequencing reads," 2011, 17.1: 10-12.
Masur et al., "Myofibroblasts differentiate from fibroblasts when plated at low density," PNAS, 1996, 93 (9):4219-23.
McCurdy et al., "Cardiac extracellular matrix remodeling: fibrillar collagens and Secreted Protein Acidic and Rich in Cysteine (SPARC)," J Mol Cell Cardiol, 2010, 48 (3):544-9.
Meran and Steadman, "Fibroblasts and myofibroblasts in renal fibrosis," Int J Exp Pathol, 2011, 92 (3):158-67.
Mimura et al., "Constitutive phosphorylation of focal adhesion kinase is involved in the myofibroblast differentiation of scleroderma fibroblasts," J Invest Dermatol, 2005, 124 (5):886-92.
Mitra et al., "Focal adhesion kinase: in command and control of cell motility," Nat Rev Mol Cell Biol, 2005, 6 (1):56-68.
Nanthakumar et al., "Dissecting fibrosis: therapeutic insights from the small-molecule toolbox," Nat Rev Drug Discov, 2015, 14 (10):693-720.
NCBI Reference Sequence: NP_001159884.1. SPARC-related modular calcium-binding protein 2 isoform 2 precursor [*Homo sapiens*] (Dec. 24, 2015) [Retrieved from the Internet Jun. 4, 2017:<https://www.ncbi.nlm.nih.gov/protein/262050673?sat=4&satkey=155517297>]; in entirety.
Pazin and Albrecht, "Developmental expression of Smoc1 and Smoc2 suggests potential roles in fetal gonad and reproductive tract differentiation," Dev Dyn, 2009, 238 (11):2877-90.
Rocnik et al., "The novel SPARC family member SMOC-2 potentiates angiogenic growth factor activity," J Biol Chem, 2006, 281 (32):22855-64.
Sasaki et al., Crystal structure and mapping by site-directed mutagenesis of the collagen-binding epitope of an activated form of BM-40/SPARC/osteonectin, EMBO J, 1998, 17 (6):1625-34.
Schellings et al., "Matricellular proteins in the heart: possible role during stress and remodeling," Cardiovasc Res, 2004, 64 (1):24-31.
Schena and Gesualdo, "Pathogenic Mechanisms of Diabetic Nephropathy," J. Am. Soc. Nephrol, 2005, 16: S30-33.
Supek et al., "REVIGO summarizes and visualizes long lists of gene ontology terms," PLoS One, 2011, 6(7):e21800.
Tomasek et al., "Myofibroblasts and mechano-regulation of connective tissue remodeling," Nat Rev Mol Cell Biol, 2002, 3 (5):349-63.
Whaley-Connell and Sowers, "Chronic Kidney Disease and the Cardiometabolic Syndrome," J. Clin, Hypert, 2006, 8(4): 546-48.
Wong and Rustgi, "Matricellular proteins: priming the tumour microenvironment for cancer development and metastasis," Br J Cancer, 2013, 108 (4):755-61.
EP Extended European Search Report in European Appln. No. 17757080.1, dated Sep. 18, 2019, 7 pages.
Geraduzzi et al., "Silencing SMOC2 ameliorates kidney fibrosis by inhibiting fibroblast to myofibroblast transformation," JCI Insight, Apr. 2017, 2(8): e90299, 18 pages.
Sugimoto et al., "Activin-like kinase 3 is important for kidney regeneration and reversal of fibrosis", Nature Medicine, Feb. 2012, 18(3):396-404.
JP Office Action in Japanese Appln No. 2018-544927, dated Feb. 24, 2021, 8 pages (with English translation).
EP Office Action in EP Appln. No. 17757080, dated Aug. 28, 2020, 5 pages.
Petersen et al., "Oral administration of GW788388, an inhibitor of TGF-β type I and II receptor kinases, decreases renal fibrosis," Kidney International, Mar. 2008,73(6):705-715.

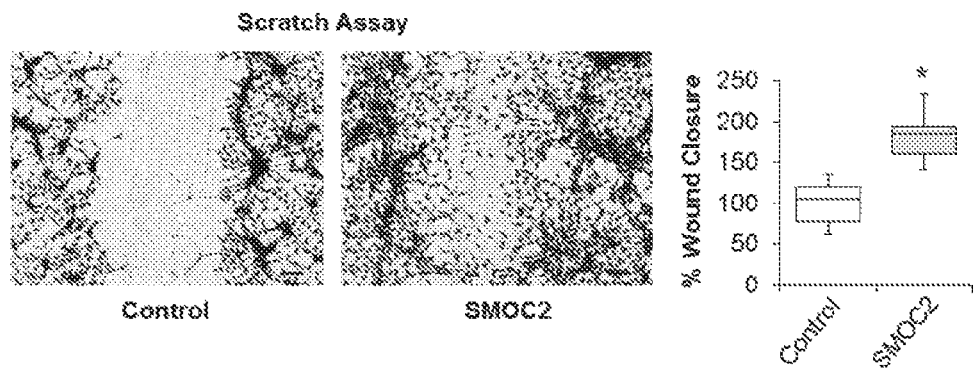
FIG. 3I
FIG. 3J
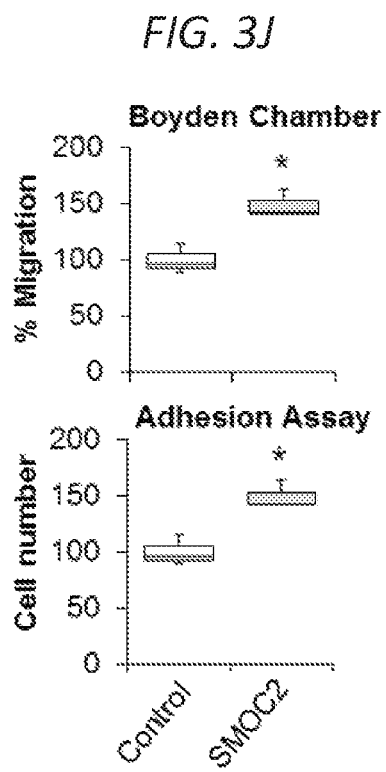
FIG. 3K

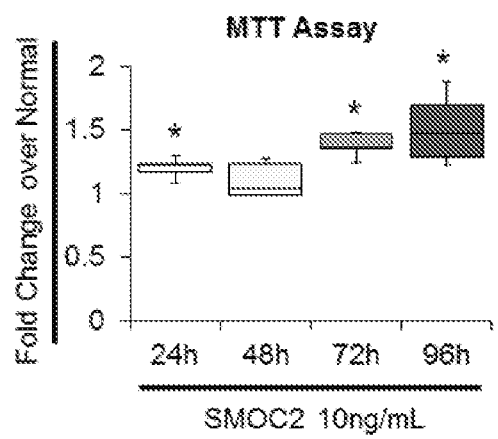
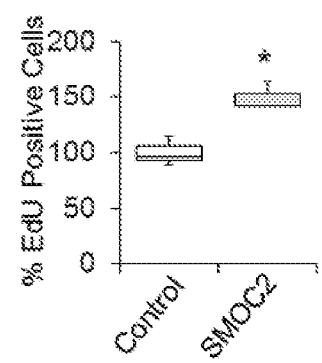
FIG. 3L    FIG. 3M
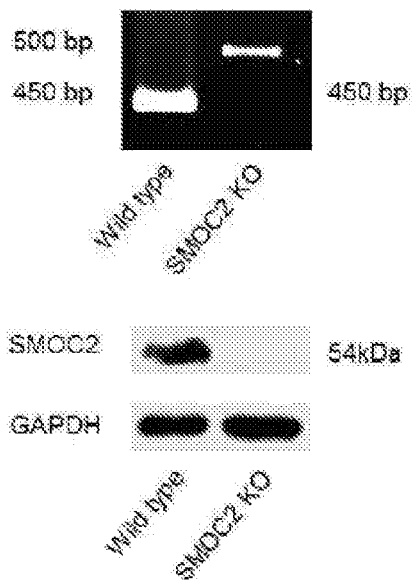
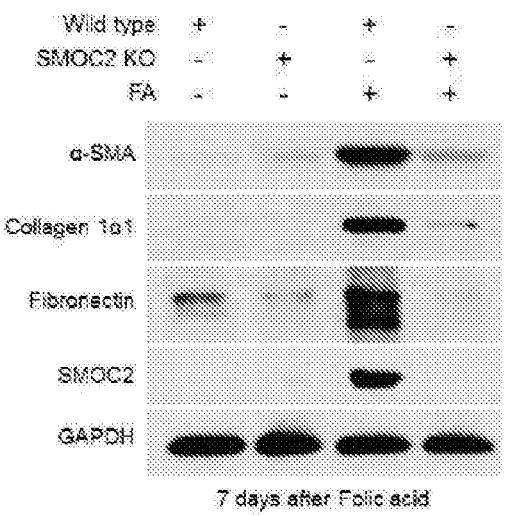
FIG. 4A    FIG. 4B

TREATMENT METHODS FOR FIBROSIS TARGETING SMOC2

CLAIM OF PRIORITY

This application is a § 371 National Stage Application of PCT/US2017/018753, filed Feb. 21, 2017, which claims the benefit of U.S. Provisional Application Ser. No. 62/299,618, filed on Feb. 25, 2016. The entire contents of the foregoing are incorporated herein by reference.

FEDERALLY SPONSORED RESEARCH OR DEVELOPMENT

This invention was made with Government support under Grant No. ES017543 awarded by the National Institutes of Health. The Government has certain rights in the invention.

TECHNICAL FIELD

Described herein are methods for treating fibrosis, e.g., kidney fibrosis, using agents that target Secreted Modular Calcium-binding protein 2 (SMOC2).

BACKGROUND

Fibrosis is an aberrant repair response to chronic tissue injury (1). The fairly conserved mechanism of repair makes fibrosis a common end-feature of nearly all chronic inflammatory organ diseases, contributing to the morbidity and mortality of approximately half of the industrialized world (1). The kidney is known for its high susceptibility to injury related, in part, to its elevated concentrations of filtered toxins and predisposition to ischemia as well as sepsis rendering it particularly susceptible to fibrosis (2).

SUMMARY

Secreted MOdular Calcium-binding protein 2 (SMOC2) belongs to the SPARC (Secreted Protein Acidic and Rich in Cysteine) family of matricellular proteins whose members are known to modulate cell-matrix interactions. As reported herein, SMOC2 is upregulated in the kidney tubular epithelial cells of mice and humans following fibrosis. Using genetically manipulated mice with SMOC2 overexpression or knockdown, SMOC2 was shown to be critically involved in the progression of kidney fibrosis. Without wishing to be bound by theory, the results suggest that mechanistically, SMOC2 activates a fibroblast-to-myofibroblast transition (FMT) to stimulate stress fiber formation, proliferation, migration and extracellular matrix production. Furthermore, targeting SMOC2 by siRNA resulted in attenuation of TGFβ1-mediated FMT in vitro and an amelioration of kidney fibrosis in mice. These findings implicate SMOC2 as a key signaling molecule in the pathological secretome of a damaged kidney, and targeting SMOC2 offers a novel therapeutic strategy for inhibiting FMT mediated kidney fibrosis.

Thus, provided herein are methods for treating a subject who has kidney fibrosis, the method comprising administering to the subject a therapeutically effective amount of an inhibitor of Secreted Modular Calcium-binding protein 2 (SMOC2). Also provided are inhibitors of Secreted Modular Calcium-binding protein 2 (SMOC2) for use in treating kidney fibrosis in a subject.

In some embodiments, the inhibitor is a monoclonal antibody or antigen binding portion thereof that binds specifically to SMOC2.

In some embodiments, the monoclonal antibody or antigen binding portion thereof is chimeric, humanized, or fully human.

In some embodiments, the inhibitor is an inhibitory nucleic acid that targets a SMOC2 transcript.

In some embodiments, the inhibitory nucleic acid is selected from the group consisting of antisense oligonucleotides, small interfering RNAs (siRNAs), small hairpin RNAs (shRNAs).

In some embodiments, the inhibitory nucleic acid is modified, e.g., comprises a modified backbone, e.g., an amide or morpholino backbone, or comprises one or more modified nucleosides, e.g., comprises at least one locked nucleoside.

In some embodiments, the subject has chronic kidney disease, metabolic syndrome, vesicoureteral reflux, tubulointerstitial renal fibrosis, diabetes (including diabetic nephropathy), and glomerular nephritis (GN).

In some embodiments, the GN is focal segmental glomerulosclerosis and membranous glomerulonephritis or mesangiocapillary GN.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 3H-M. SMOC2 induces the properties of myofibroblast activities. (H) REVIGO treemap visualization for highly similar GO terms describing 'biological processes' significantly different between SMOC2 Tg and WT mice. (I) Scratch assay performed on NIH3T3 cells treated 24 h with 10 ng/ml SMOC2. Healing percentage represented in graph (n=5, 3 visual fields/condition; 10× magnification, 50 μM). (J) Boyden Chamber assay performed on NIH3T3 cells treated 24 h with 10 ng/ml SMOC2. (K) NIH3T3 cells were treated 24 h with/out 10 ng/mL SMOC2, then trypsinized and reseeded. After 1 h, unattached cells were washed and cell numbers were quantified for adherence (n=3). (L) Metabolic activity of control and 10 ng/mL SMOC2 treated NIH3T3 cells were measured over time by MTT assay (n=5). (M) NIH3T3 fibroblasts were treated 24 h with/out 10 ng/ml SMOC2 and cell proliferation was assessed by EdU labeling and fluorescence-activated cell sorting (FACS) (n=5). Box plots describe the median (line within box), upper and lower quartiles (bounds of box), and minimum and maximum values (bars). *P<0.05 determined by t-test.

FIGS. 4A-D. Genetic inhibition of SMOC2 limits folic acid-induced kidney fibrosis in mice. (A) Confirmation of SMOC2 deletion in SMOC2 knockout (SMOC2 KO) mice by PCR (above, PCR primers specific to recognize knock-in insert) and Western blotting (below). (B) Representative Western blot (n=4/group; densitometry in FIG. 14) of αSMA, collagen 1α1, fibronectin and SMOC2 expression using kidney samples obtained at day 7 from SMOC2 KO and Wild type (WT) mice subjected to Folic acid (FA) treatment. (C) Immunofluorescent αSMA staining of KO and WT kidneys at baseline and day 7 following FA treatment (n=4/group). (D) Masson's Trichrome staining of normal and FA treated kidneys obtained at day 7 from KO and WT mice. Quantification of images is represented as box plots (n=4/condition, 10 visual fields/mice), which describe the median (line within box), upper and lower quartiles (bounds of box), and minimum and maximum values (bars). *P<0.05 (WT normal) and #P<0.05 (WT at respective treatment) determined by one-way analysis of variance (ANOVA) with Tukey post-hoc analysis.

Scheme of the experimental procedure for SMOC2 siRNA or ssiRNA injected C57BL/6 mice treated with/out Folic acid (FA). Mice were injected intravenously with 30 μg/200 uL of SMOC2 siRNA or ssiRNA 4 h before and 2, 4 and 6 days after an intraperitoneal injection of 250 mg/kg of FA. Representative Western blot (n=5/group; densitometry in FIG. 19) was performed for SMOC2, αSMA, collagen 1α1 and fibronectin. (C) Immunofluorescent αSMA staining of kidneys obtained from mice at baseline and at day 7 following FA either treated with ssiRNA or SMOC2 ssiRNA (n=5). (D) Masson's Trichrome staining of normal and FA treated kidneys obtained at day 7 following ssiRNA or SMOC2 siRNA administration. Confocal and Light microscopy images are 20× magnification; Scale bars, 50 μM. Quantification of images is represented as a box plot (n=5/condition, 10 visual fields/mice), which describe the median (line within box), upper and lower quartiles (bounds of box), and minimum and maximum values (bars). *P<0.05 (ssiRNA+vehicle) and #P<0.05 (ssiRNA respective treatment) determined by one-way analysis of variance (ANOVA) with Tukey post-hoc analysis.

FIGS. 7A-D. Quantitation of SMOC2 protein expression along with fibrotic markers. FA treated mice SMOC2 levels by (A) qPCR and (B) Western blot. Mice were (C) subjected to Unilateral Ureteral Obstruction (UUO) or (D) treated with Folic Acid (FA), intraperitoneally, then sacrificed at 7 days and 14 days. Western blotting was performed on kidney tissue lysates to measure established fibrotic markers such as α-smooth muscle actin (αSMA), collagen 1α1 and fibronectin. For the UUO model, Contralateral Kidney (CoK) tissue lysates were also included. Densitometry data are representative of Western blot images from FIG. 1B (UUO) and FIG. 1C (FA) which were normalized to sham/vehicle and represent mean±SEM (n=5 mice/group/time point). *P<0.05 determined by t-test.

Figure 8A:
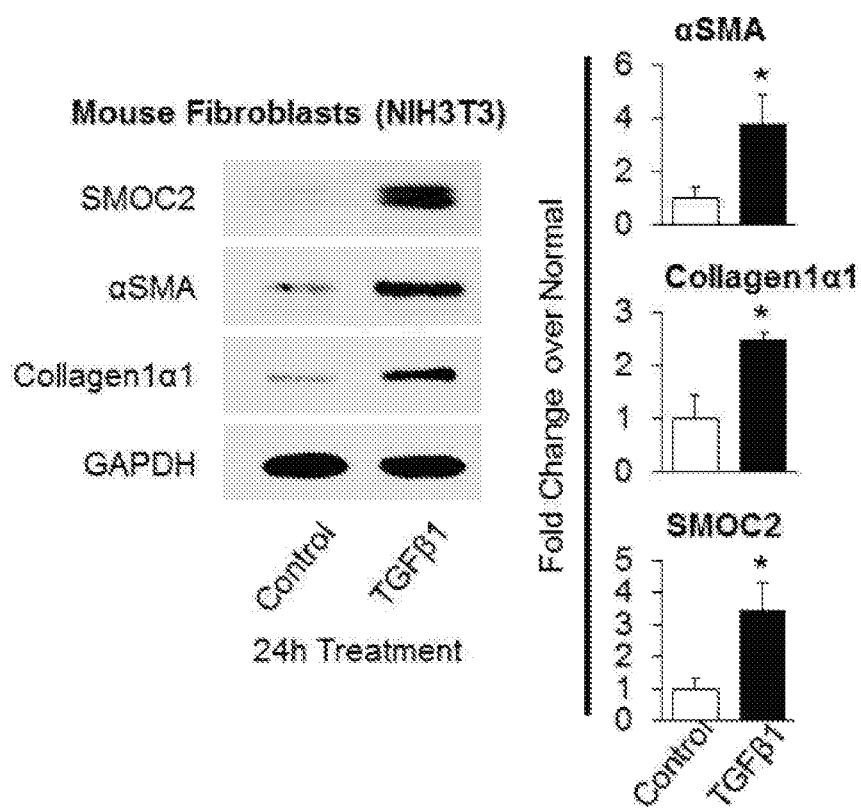
Figure 8B:
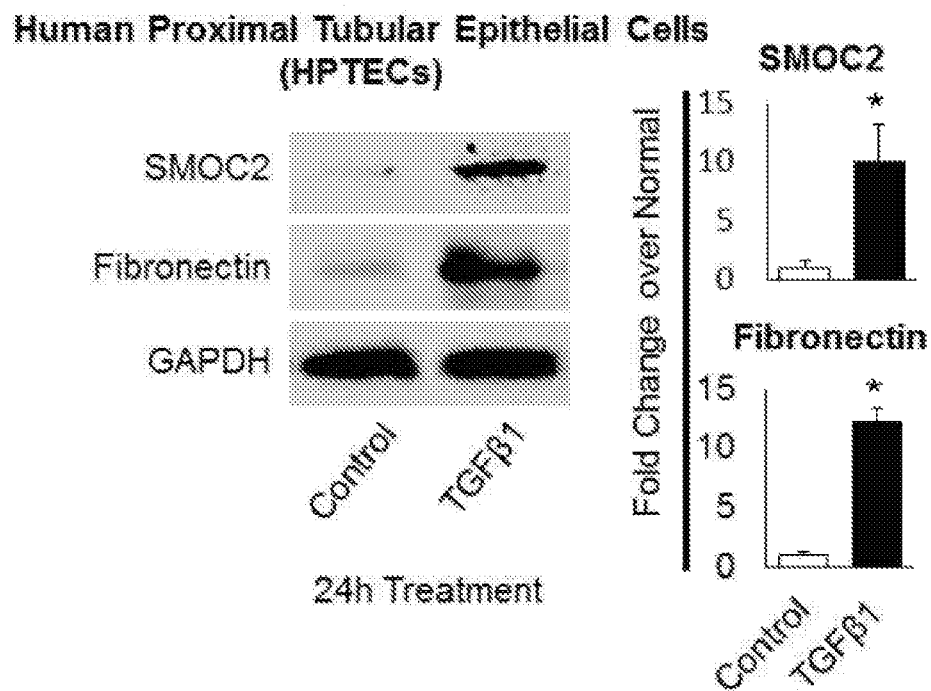

FIGS. 8A-B. TGFβ1 induces the expression of SMOC2 in fibroblasts and epithelial cells. NIH3T3 (A, n=4) and HPTEC cells (B, n=3) were incubated with 10 ng/mL TGFβ1 for 24 h. Protein expression of listed targets was determined by Western blot. Densitometry data are relative to control levels, normalized by GAPDH and represent Mean±SEM. *P<0.05 determined by t-test.

Figure 2A:
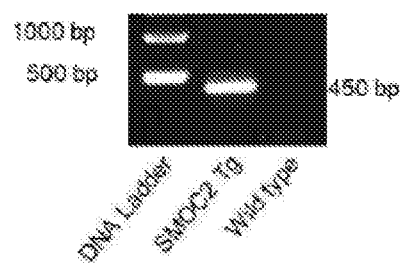
FIGS. 2A-G. SMOC2-overexpressing mice are more susceptible to kidney fibrosis than Wild type mice. (A) Confirmation of SMOC2 overexpression in SMOC2 transgenic (SMOC2 Tg) mice by PCR (above, Primers specific to recognize Tg insert) and Western blotting (below). (B) Representative Western blot (n=5/condition; densitometry in FIG. 10B) of αSMA, collagen 1α1, fibronectin and SMOC2 expression using kidney samples obtained from SMOC2 Tg and Wild type (WT) mice subjected to 7 and 14 days of Unilateral Ureteral Obstruction (UUO). (C) Immunofluorescent staining for αSMA in CoK and fibrotic kidneys from WT and SMOC2 Tg mice at day 7 following UUO (n=5/condition, 5 visual fields/tissue). (D) Western blot (n=5/condition; densitometry in FIG. 11B) of αSMA, collagen 1α1, fibronectin and SMOC2 expression using kidney samples obtained from SMOC2 Tg and Wild type (WT) mice subjected to 7 and 14 days of Folic acid (FA). (E) Immunofluorescent staining for αSMA of normal and fibrotic kidneys from WT and SMOC2 Tg mice at day 7 following FA (n=5/condition, 10 visual fields/tissue). (F) Picrosirius Red (n=5/condition, 10 visual fields/tissue) and Masson's Trichrome (n=5/condition, 5 visual fields/tissue) staining of CoK versus 7 and 14 day UUO treated kidneys. (G) Picrosirius Red and Masson's Trichrome staining of normal versus 7 and 14 day FA treated kidneys (n=5/condition, 5 visual fields/tissue). Confocal and Light microscopy images were 20× magnification. Relative quantifications of images are represented as box plots, which describe the median (line within box), upper and lower quartiles (bounds of box), and minimum and maximum values (bars). *P<0.05 (CoK (UUO) or Normal (FA)) and #P<0.05 (WT at respective time point) determined by one-way analysis of variance (ANOVA) with Tukey post-hoc analysis.
Figure 2A:
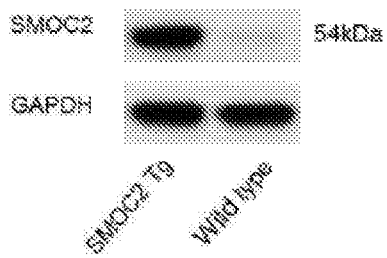
Figure 2B:
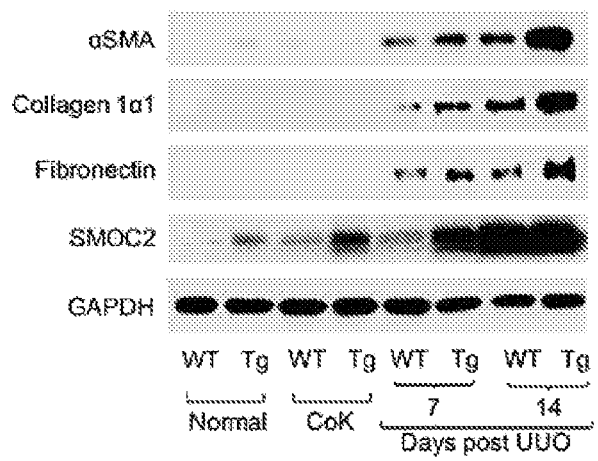
Figure 9A:
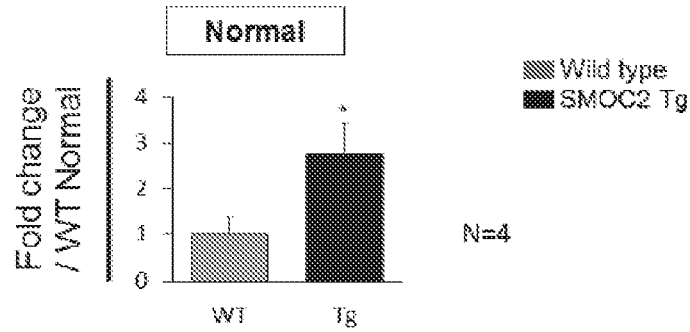
Figure 9B:
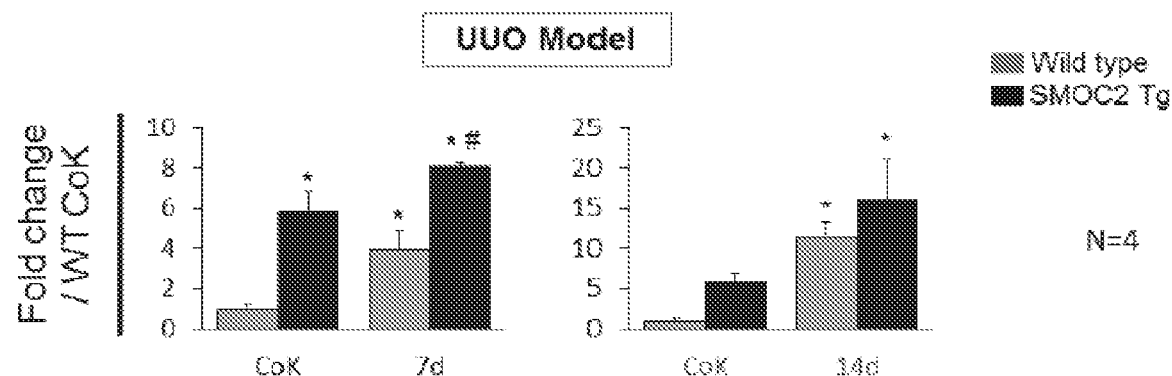
Figure 9C:
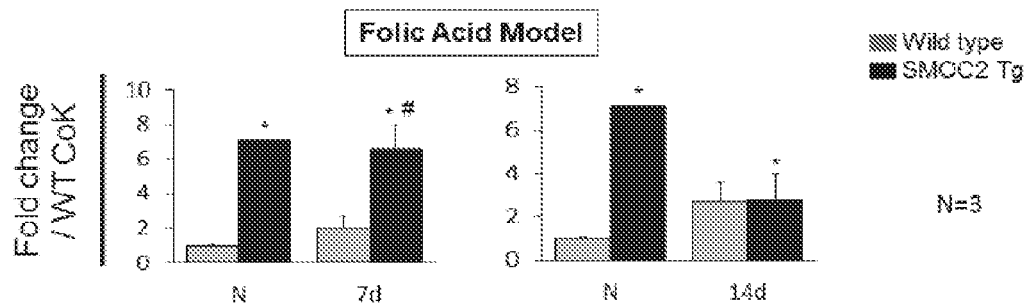

FIGS. 9A-C. Quantitation of SMOC2 protein expression along with fibrotic markers in wild type and SMOC2 transgenic mice. (A) Densitometry for SMOC2 expression in SMOC2 Tg and wild type (WT) mice (n=4). (B) SMOC2 Tg and wild type (WT) mice were subjected to Unilateral Ureteral Obstruction (UUO), and protein expression from kidney tissue samples collected at 7 and 14 days following UUO were assessed by Western blot for SMOC2. (C) SMOC2 Tg and WT mice treated with Folic Acid (FA) and protein expression of αSMA, collagen 1α1, fibronectin and SMOC2 was assessed by Western blot from kidney tissue samples collected at 7 and 14 days post FA. Densitometry are representative of Western blot images from FIG. 2B (UUO) and FIG. 2D (FA) which were normalized to sham/vehicle and represent mean±SEM (n=3-4 mice/group/time point). *P<0.05 determined by t-test.

Figure 10A:
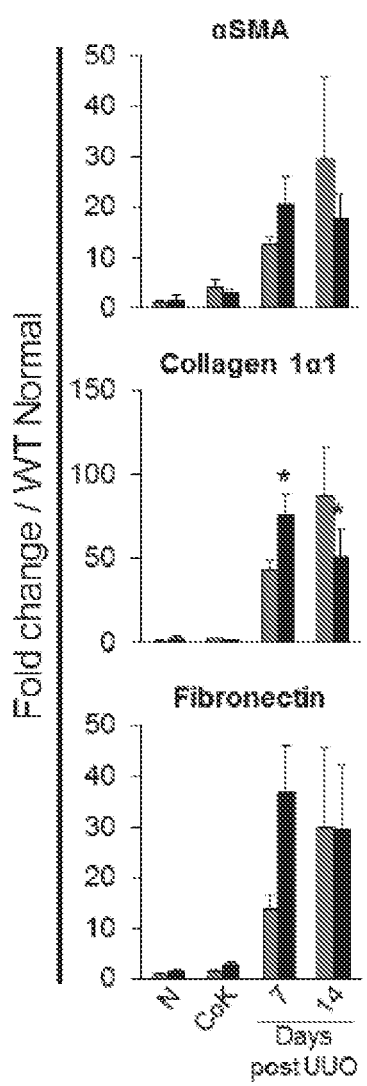
Figure 10B:
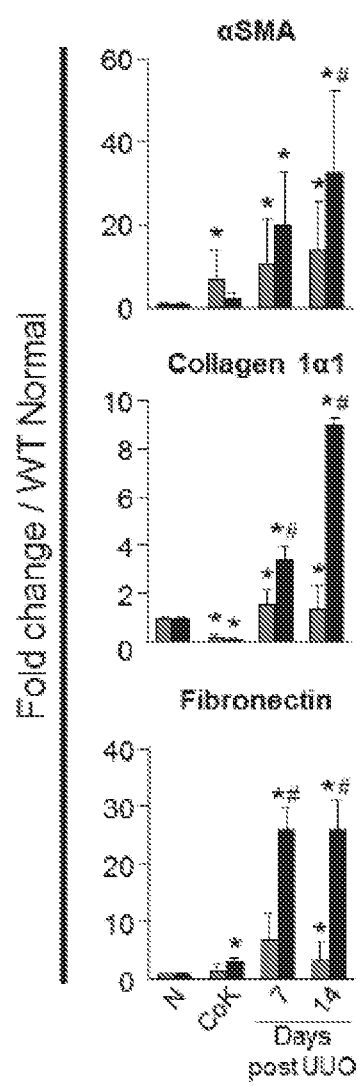

FIGS. 10A-B. Quantitation of SMOC2 mRNA and protein levels along with fibrotic markers in mice following Unilateral Ureteral Obstruction. SMOC2 Tg and Wild type (WT) mice were subjected to Unilateral Ureteral Obstruction (UUO) then sacrificed at 7 and 14 days. (A) Quantitative rtPCR and (B) Western blot analysis were performed on kidney tissue lysates to measure the expression of αSMA, collagen 1α1, and fibronectin (Densitometry data from FIG. 2B Western blots). Contralateral Kidney (CoK) tissue lysates were also included. The expression was normalized to housekeeping gene GAPDH and values are represented as fold change over WT normal. Mean±SEM (n=5 mice/group/time point). *P<0.05 (WT Normal) and #P<0.05 (WT at respective time point) determined by one-way analysis of variance (ANOVA) with Tukey post-hoc analysis.

Figure 11A:
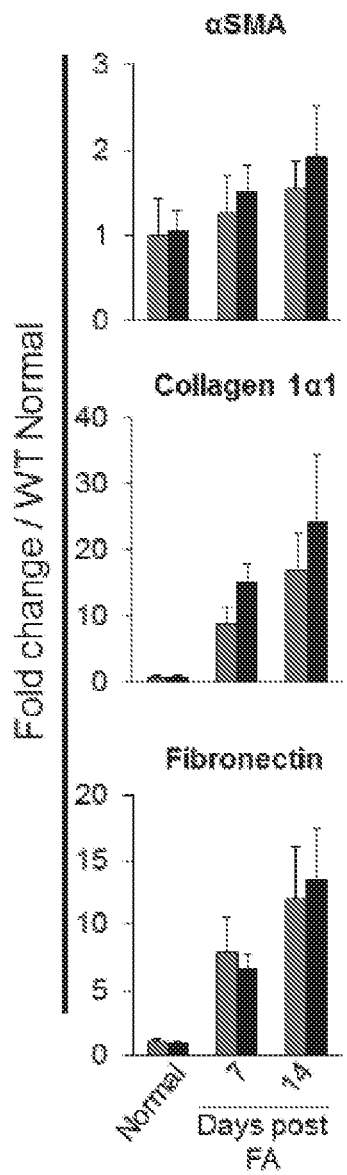
Figure 11B:
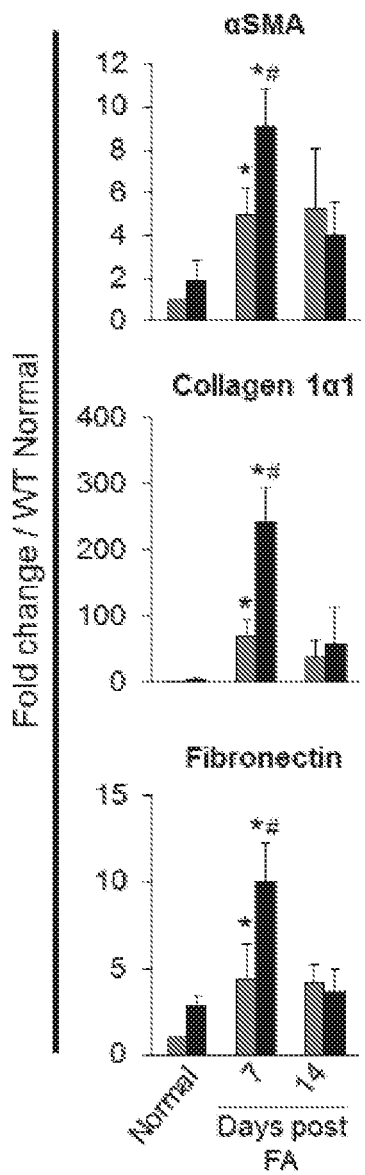

FIGS. 11A-B. Quantitation of SMOC2 mRNA and protein levels along with fibrotic markers in mice following Folic acid administration. SMOC2 Tg and Wild type (WT) mice were subjected to Folic acid (FA), intraperitoneally, treatment then sacrificed at 7 and 14 days. (A) Quantitative rtPCR and (B) Western blot analysis were performed on kidney tissue lysates to measure the expression of αSMA, collagen 1α1, and fibronectin (Densitometry data from FIG. 2D Western blots). Quantitative data are relative to WT normal levels, normalized by GAPDH. Mean±SEM (n=5 mice/group/time point). *P<0.05 (WT Normal) and #P<0.05 (WT at respective time point) determined by one-way analysis of variance (ANOVA) with Tukey post-hoc analysis.

Figure 3A:
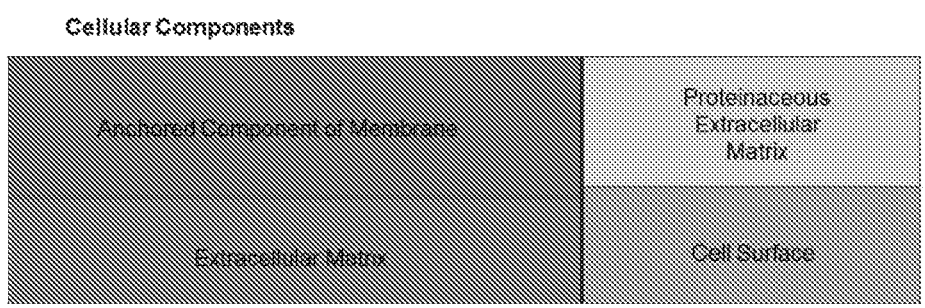
FIGS. 3A-G. SMOC2 induces a fibroblast-to-myofibroblast transition. (A) RNAseq was performed using kidneys from SMOC2 Tg and WT mice at day 7 following UUO treatment. REVIGO treemap visualizations are shown for enriched gene ontology (GO) categories. Highly similar GO terms for 'cellular components' are grouped together and visualized by different colors and sizes of the rectangles using semantic similarity and enrichment p-values. Western blots of αSMA, collagen 1α1 and fibronectin from serum deprived primary human kidney fibroblasts (B, n=3/condition; densitometry in FIG. 12C) and NIH3T3 fibroblasts (C, n=3/condition; densitometry in FIG. 12D) treated with 10 ng/mL SMOC2 with/out TGFβ1. (D) After 1 h antibody pretreatment, SMOC2 or TGFβ1 was treated to serum deprived NIH3T3 cells for 24 h then tested for conventional fibrotic markers, while integrin β1 antibody was pretreated with NIH3T3 cells then treated with SMOC2 (n=3/condition; densitometry in FIG. 12E). (E) NIH3T3 fibroblasts were transfected with SMOC2-MYC, empty vector control or negative control MGP-MYC then immunoprecipitated with a MYC-(above) or Integrin-antibody (below). Western blots of representative immunoprecipitation experiments. (F) Representative Western blot for Phospho(P)-Focal Adhesion Kinase (FAK) Y925, P-Myosin Light Chain (MLC) Ser19 and P-Paxillin Tyr118 from NIH3T3 cells treated with 10 ng/mL SMOC2 or 5 ng/mL TGFβ1 for 60 minutes (n=5/condition; densitometry in FIG. 12H). (G) Phalloidin staining of F-Actin after NIH3T3 cells were treated 24 h with 10 ng/mL SMOC2 or 5 ng/mL TGFβ1 (n=3). Box plots describe the median (line within box), upper and lower quartiles (bounds of box), and minimum and maximum values (bars). *P<0.05 determined by t-test.
Figure 3B:
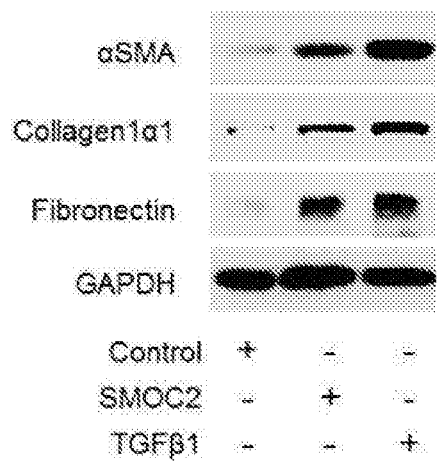
Figure 3C:
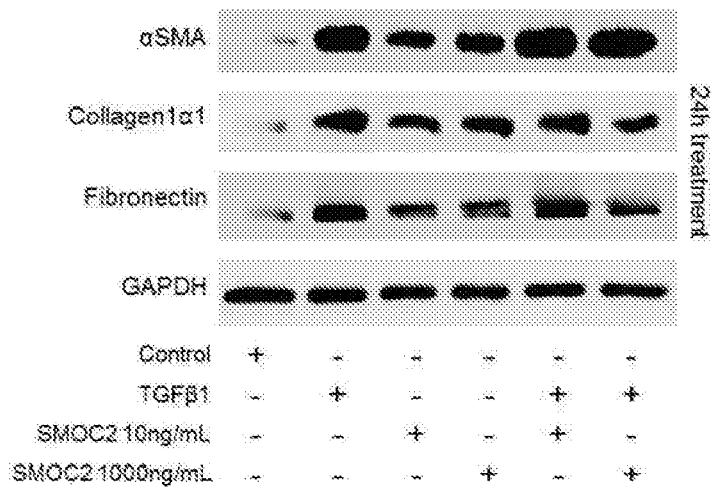

FIGS. 12A-J. In vitro profile of recombinant SMOC2 on NIH3T3 cells. (A) Serum deprived NIH3T3 cells treated with varying concentrations of SMOC2 for 24 h and measured for αSMA, collagen 1α1 and fibronectin expression by Western blot. (B) Western blot images with respective densitometry (n=4) showing fibrotic markers from quiescent primary human kidney fibroblasts treated with 10 ng/mL SMOC2 or 5 ng/mL TGFβ1 for 24 h. (C) Densitometry data for FIG. 3B showing 48 h SMOC2 treatment on primary human kidney fibroblasts (n=3). (D) Compared to profibrotic TGFβ (long/mL), densitometry data for FIG. 3C Western blots show the expression levels of myofibroblast markers αSMA, collagen 1α1 and fibronectin from serum deprived NIH3T3 fibroblasts treated for 24 h with 10 ng/mL SMOC2 (n=3). (E) Densitometry data representing FIG. 3D (n=3) antibody blocking. (F) Antibody blocking titration of SMOC2 treated NIH3T3 cells. (G) Western blot images with respective densitometry (H) showing phosphoactivating profibrotic signals Phospho(P)-Focal Adhesion Kinase (FAK) Y925, P-Myosin Light Chain (MLC) Ser19 and P-Paxillin Tyr118 from quiescent NIH3T3 fibroblasts treated with 10 ng/mL SMOC2 or 5 ng/mL TGFβ1 for 45 min (H left, densitometry; n=5) and 60 minutes (H right, densitometry data from FIG. 3F Western blots; n=5). (J) Quantification of the NIH3T3 cell density into the wound area of a migration assay over a time course. (K) Metabolic activity of NIH3T3 cells treated with various concentrations of SMOC2 over a time course were measured by MTT assay (n=5). Densitometry data are relative to control levels, normalized by GAPDH and represent Mean±SEM. *P<0.05 determined by t-test. #P<0.05 (Control at respective time point).

FIGS. 13A-G SMOC2 transfected fibroblasts acquire an active phenotype. Quantification of RNA expression (A) and protein expression (B) of SMOC2 by rtPCR and Western blot in pCMV and pCMV-SMOC2 transfected NIH3T3 cells. Quantitative rtPCR and densitometry data are relative to pCMV control levels, normalized by GAPDH and represent Mean±SEM (RNA n=3, 2 technical replicates; Protein n=3). (C) Metabolic activity of pCMV control and pCMV-SMOC2 transfected NIH3T3 cells were measured by MTT assay over listed days (n=12/time point, % relative to day 1). (D) The wound healing influence of SMOC2 transfection on fibroblasts was analyzed by a scratch assay. Equally dispersed cells were inflicted with a scratch to evaluate the restorative capacity between the 24 h post-SMOC2 transfected NIH3T3 cells and its pCMV control. The difference in healing was calculated as a percentage of pCMV-SMOC2 over pCMV transfected cells. Representative images (10×; scale bar=50 μM) were stained with methylene blue at 24 h for increased contrast. (E) NIH3T3 cells were transfected with pCMV or pCMV-SMOC2 for 24 h. Cell proliferation and cell cycle progression were measured by EdU labeling and subsequent cell cycle analysis by fluorescence-activated cell sorting (FACS). (F) The migration potential of SMOC2 transfected NIH3T3 cells was evaluated using the Boyden Chamber assay to determine the percentage of migrating cells. (G) NIH3T3 cells were transfected with pCMV and pCMV-SMOC2 for 24 h, after which cells were harvested by trypsin and reseeded. After 1 h, unattached cells were washed and cell numbers were quantified for adherence (n=3). *P<0.05 determined by t-test.

Figure 14:
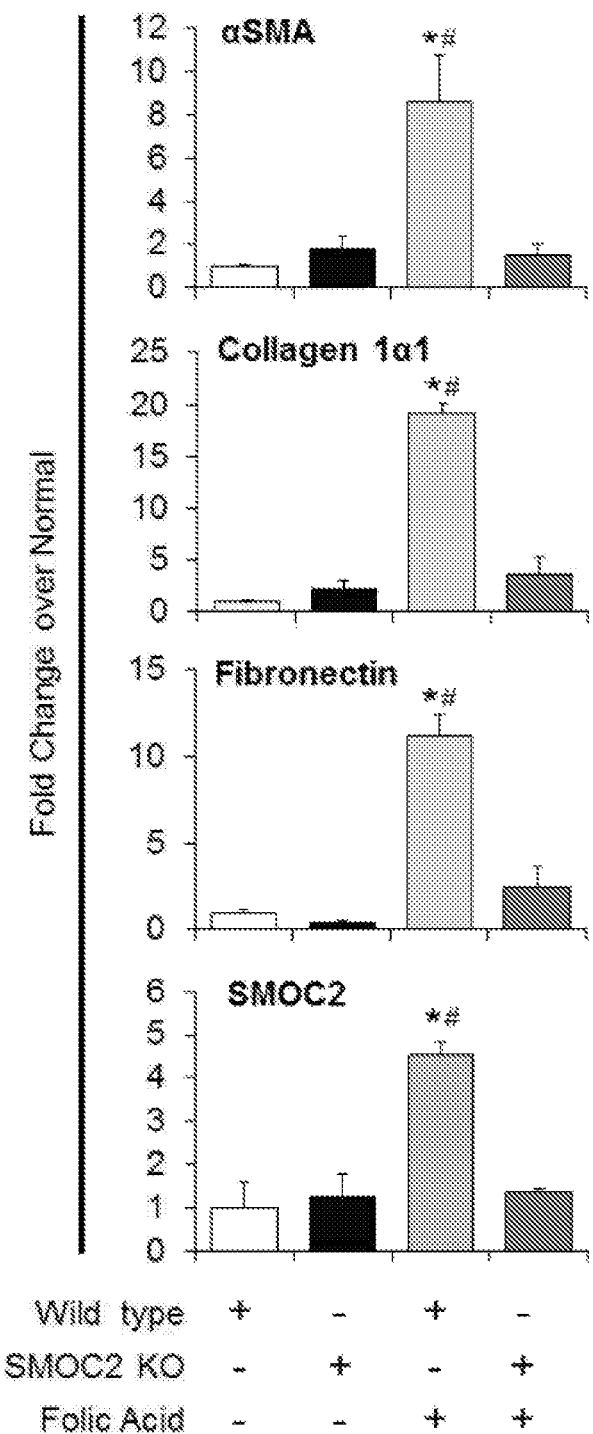

FIG. 14 Quantitation of Western blots for fibrotic markers in SMOC2 knockout (KO) and wild type mice treated with folic acid. Densitometry data representing FIG. 5B which is relative to normal Wild type (WT) mice, normalized to GAPDH and represent Mean±SEM (n=4). *P<0.05 (normal WT) and #P<0.05 (WT at respective treatment) determined by one-way analysis of variance (ANOVA) with Tukey post-hoc analysis.

Figure 15:
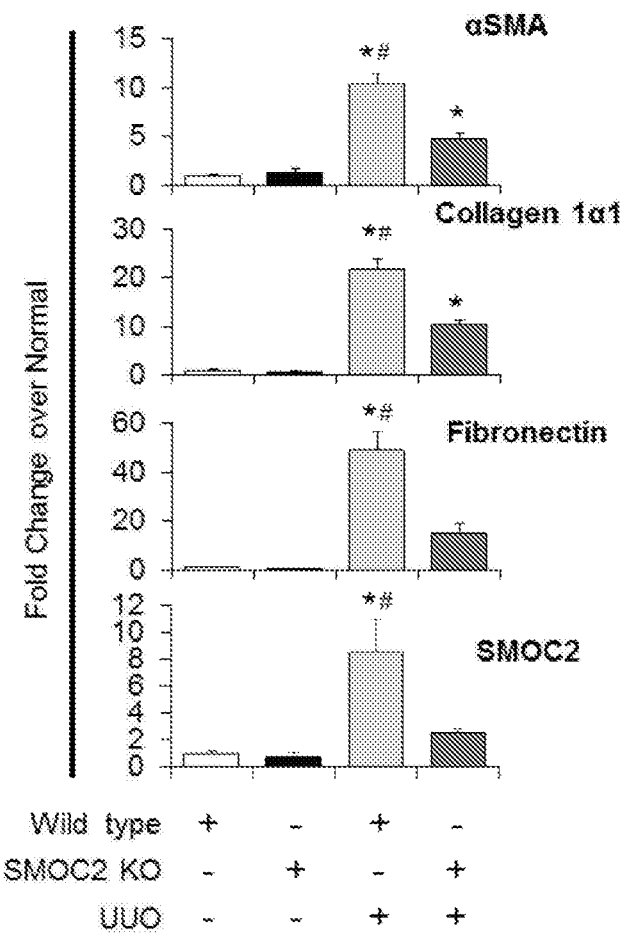

FIG. 15. Quantitation of Western blots for SMOC2 and fibrotic markers in SMOC2 knockout (KO) and Wild type mice that underwent UUO surgery. Densitometry data representing FIG. 6A which is relative to Wild type (WT) CoK mice, normalized to GAPDH and represent Mean±SEM (n=5). *P<0.05 (WT CoK) and #P<0.05 (WT at respective treatment) determined by one-way analysis of variance (ANOVA) with Tukey post-hoc analysis.

Figure 16:
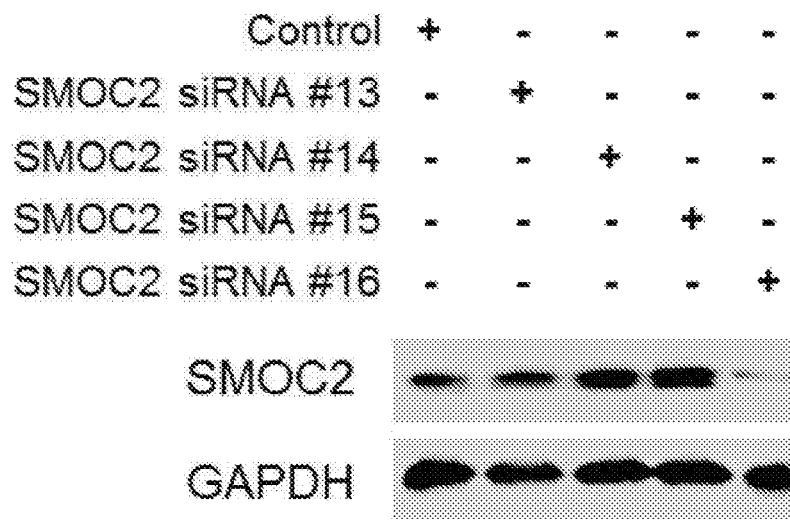

FIG. 16. Performance of SMOC2 siRNAs in NIH3T3 cells. NIH3T3 cells treated with various SMOC2 siRNA for 24 h and measured for SMOC2 production by Western blot.

Figure 17:
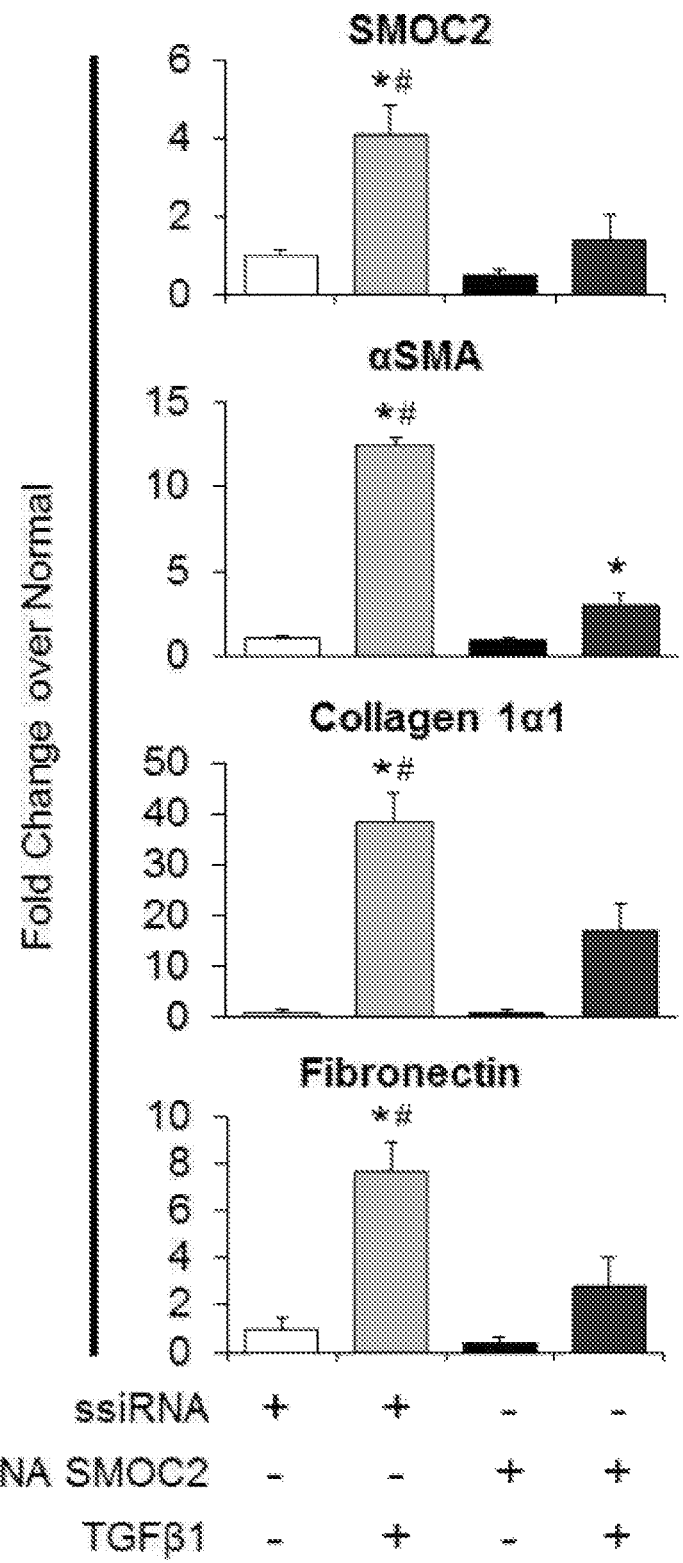

FIG. 17. Quantitation of Western blots for SMOC2 siRNA treatment of fibroblasts. Densitometry data representing FIG. 7A which is relative to untreated ssiRNA transfected NIH3T3 cells, normalized by GAPDH and represent Mean±SEM (n=3). *P<0.05 (untreated ssiRNA cells) and #P<0.05 (ssiRNA cells at respective treatment) determined by one-way analysis of variance (ANOVA) with Tukey post-hoc analysis.

Figure 18:
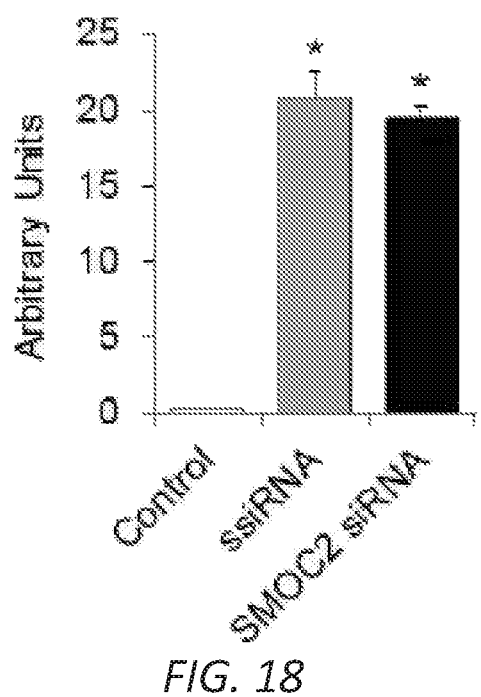

FIG. 18 Enrichment of siRNA in the mice kidneys following iv injection via the tail vein. Mice were injected intravenously with 30 μg/200 uL of SMOC2 siRNA or ssiRNA 4 h before and 2, 4 and 6 days and sacrificed on day 7. siRNA oligonucleotides were synthesized as Fluorescein conjugate; hence, visualized to evaluate siRNA delivery by 40× and 20× confocal microscopy. Images were representative of 10 visual fields/mouse (n=5 mice/group). Quantification is represented in a bar graph as arbitrary units (Mean±SEM, n=5 mice/group, 10 visual fields/mice).

Figure 19:
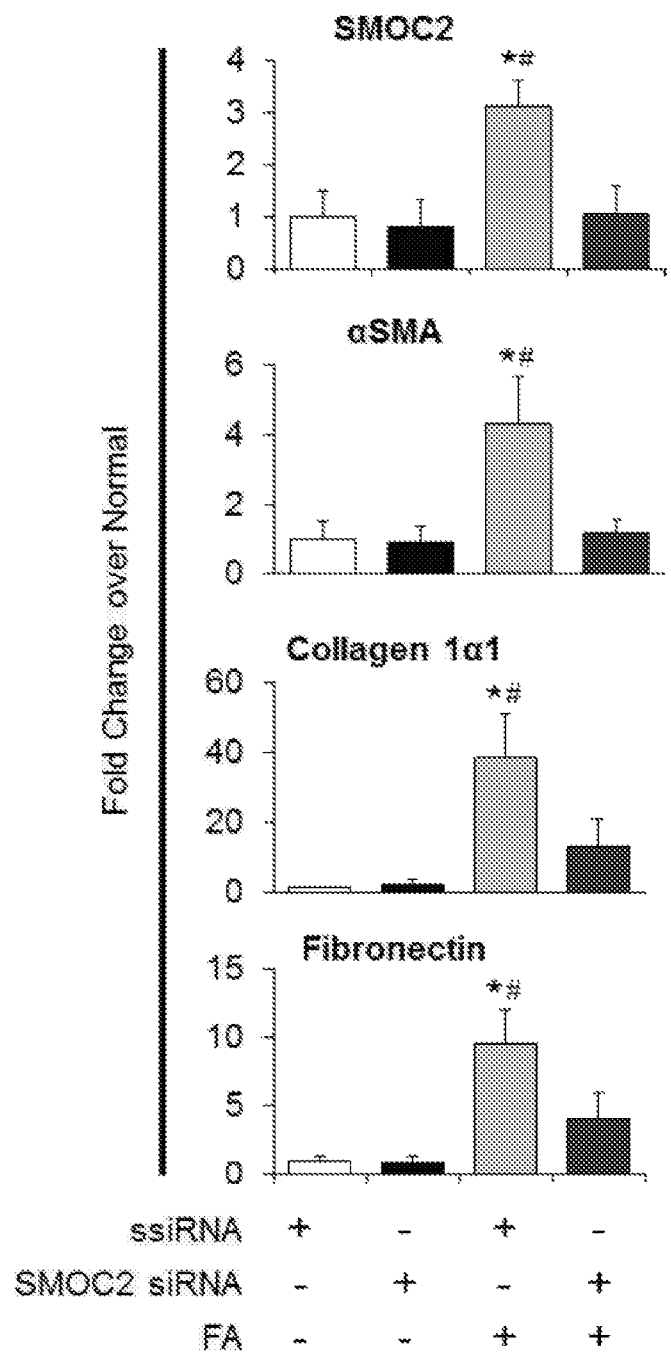

FIG. 19. Quantitation of Western blots for mice treated with SMOC2 siRNA followed by folic acid administration. Densitometry data representing FIG. 7B which are relative to untreated ssiRNA injected mice, normalized to GAPDH and represent Mean±SEM (n=5). *P<0.05 (ssiRNA normal) and #P<0.05 (ssiRNA at respective treatment) determined by one-way analysis of variance (ANOVA) with Tukey post-hoc analysis.

DETAILED DESCRIPTION

Kidney fibrosis is the common pathophysiological phenomenon of a majority of progressive chronic kidney diseases (3, 4). The fibrotic events in the kidney are specifically defined by the excessive deposition of a pathological extracellular matrix (ECM) in the interstitial space between tubules and peritubular capillaries, interfering with their normal exchange of toxins and nutrients (5). Myofibroblasts are widely recognized as the effector cells responsible for fibrosis since they are considered the dominant ECM-producing cells originating via activation of resident fibroblasts by exposure to profibrotic factors, essentially TGFβ1 and ECM proteins (6-9). Inhibiting factors that regulate this self-perpetuating loop of ECM production and myofibroblast activation represents a logical approach to target kidney fibrosis that remains an unmet medical need.

Using RNA sequencing, Secreted MOdular Calcium-binding protein 2 (SMOC2) was identified as amongst the most highly upregulated genes in the kidneys of mice subjected to folic acid-induced chronic progressive kidney fibrosis (10 and WO2015/138532, published Sep. 17, 2015); however, whether this upregulation was detrimental or protective was not previously known. SMOC2 belongs to the SPARC (Secreted Protein Acidic and Rich in Cysteine) family of matricellular proteins whose members are known for their secretion into the extracellular space to not only interact with structural matrix proteins but also with cell surface receptors, growth factors, proteases and other bioactive effectors to modulate cell-matrix interactions and cell function (11). Mechanistically, apart from its role in extracellular matrix assembly signaling, SMOC2 has been hypothesized to serve as a target for controlling angiogenesis in tumor growth and myocardial ischemia (12, 13). Given that there is no information on the functional significance of SMOC2 upregulation following kidney damage, the objective of this study was to investigate whether induction of SMOC2 in the kidney regulates initiation and progression of kidney fibrosis and whether genetic or pharmacologic modulation of SMOC2 is capable of preventing fibrosis.

The stroma's composition and organization of ECM proteins are integral signaling features that dictate the cause and effect of persistent fibroblast activation, underlying pathological fibrosis (19) and, as a result, the ongoing loss of normal tissue structure. The present study systematically supports the notion that the matricellular factor SMOC2 is minimal under normal conditions but upregulated upon kidney injury to eventually partake in the deleterious response of fibrosis. We provide evidence that 1) SMOC2 expression is significantly induced in the kidneys of mice and humans following fibrosis irrespective of the mechanism of initiation of fibrosis; 2) SMOC2 is critically involved in kidney fibrosis progression because transgenic mice overexpressing SMOC2 exhibit significantly enhanced tubulointerstitial fibrosis whereas SMOC2 knockout mice are protected from kidney fibrosis development; 3) Inhibition of SMOC2 in vitro and in vivo using siRNA protects from fibrosis progression suggesting SMOC2 as a potential therapeutic target for kidney fibrosis; and 4) Mechanistically, SMOC2 activates matrix assembly signaling in the fibroblasts to stimulate stress fiber formation, proliferation, migration and ECM production—features typical of transitioning into myofibroblasts, which are the effector cells in fibrosis.

Fibroblast to Myofibroblast Transformation (FMT)

Fibroblast to myofibroblast transformation (FMT) is a quintessential phase in the development of fibrosis because of the central role myofibroblasts have in the production of collagen and fibronectin. As shown herein, SMOC2 is a key signaling molecule in the pathological secretome of a damaged kidney, whose continual presence leads to fibrosis. Without wishing to be bound by theory, as the TGFβ pathway is a hallmark pathway for FMT, we initially found that it was capable of increasing SMOC2 in vitro in fibroblasts and epithelial cells as well as discovering that SMOC2 ablation significantly attenuated TGFβ-induced FMT, making SMOC2 a potential pathological contributor to fibrosis downstream of TGFβ. Although SMOC2 has not been previously associated with any form of fibrosis, its family member SPARC has been studied extensively in multiple types of fibrosis. The level of SPARC expression was found to be increased in patients with pulmonary, kidney, hepatic and dermal fibrosis (20). Furthermore, SPARC-null mice had significantly less collagen deposition in the skin, heart, lungs and kidney upon induction of fibrotic stimuli (20). While both SPARC and SMOC2 promote fibrosis, they most probably differ in their mechanism of action to mediate the interaction between the ECM and cell. SPARC is known for its binding to collagen and post-synthetic processing and assembly of collagen into bundling structures (21, 22); however, the structure of SMOC2 lacks collagen binding sites as SPARC to mediate the same effects. This would imply a different mechanism of action whereby each SPARC member has its respective role in fibrosis development.

SMOC2

Two isoforms of SMOC2 exist in humans; the sequence of the isoform 1 precursor protein is in GenBank at NP_071421.1 (encoded by NM_022138.2), and the sequence of the isoform 2 precursor is available in GenBank at NP_001159884.1 (encoded by NM_001166412.1). Isoform 2 is shorter than Isoform 1 due to an alternate in-frame splice site in the central coding region. The RefSeqGene sequence identifier is NG_032781.1 (Range 5001-231844).

SMOC2 is expressed in the heart, muscle, spleen and ovaries (23) and its expression pattern during development suggest that it may mediate intercellular signaling and cell type-specific differentiation during gonad and reproductive tract development (24). Although we similarly detected SMOC2 expression in normal kidneys (23), overexpression of SMOC2 in mice in the absence of damage did not dispose the mouse kidney to a spontaneous fibrosis; however, the overexpression of SMOC2 in the transgenic mice accelerated a fibrotic response over the wild type only after injury. Mechanistically, SMOC2 has been shown to act on diverse cell types such as: stimulating migration and adhesion of keratinocytes through integrin (αvβ1 and αvβ6) interaction (23); on endothelial cells where SMOC2 potentiates the responses of VEGF and FGF-induced mitogenesis and angiogenesis (25); and on fibroblasts where SMOC2 regulates cell-cycle progression via integrin-linked kinase activity and cyclinD1 expression (26). Matricellular proteins are implicated in regulating the interactions between ECM components and cell surface integrins (27). Integrin αβ heterodimers translate changes in ECM signals into the fibroblast to undergo FMT (6, 28). This mechanosensitive pathway that underlies FMT can be summarized in a 3-tier cascade process using the following associated markers (14): FAK-P, MLC-P and Pax-P.

In summary, we have uncovered a novel pathway in the pathogenesis of kidney fibrosis initiated by the matricellular protein SMOC2. We show that SMOC2 is critical for the development of kidney fibrosis by stimulating matrix assembly signaling, chemotaxis and myofibroblast transitioning. We also provide compelling evidence to suggest that silencing SMOC2 to limit fibrosis holds potential as a therapeutic approach to a disease process that has yet to yield promising results.

Methods of Treatment

The methods described herein include methods for the treatment of disorders associated with kidney fibrosis. Kidney fibrosis can result from various diseases and insults to the kidneys. Examples of such diseases and insults include chronic kidney disease, metabolic syndrome, vesicoureteral reflux, tubulointerstitial renal fibrosis, diabetes (including diabetic nephropathy), and resultant glomerular nephritis (GN), including, but not limited to, focal segmental glomerulosclerosis and membranous glomerulonephritis, and mesangiocapillary GN. Since kidney fibrosis is associated with loss of blood vessels, this results in secondary ischemia which can also result in glomerular disease with loss of glomerular function. Regardless of the primary cause, insults to the kidneys may result in kidney fibrosis and the concomitant loss of kidney function. (Schena, F. and Gesualdo, L., Pathogenic Mechanisms of Diabetic Nephropathy, J. Am. Soc. Nephrol, 16: S30-33 (2005); Whaley-Connell, A., and Sower, J R., Chronic Kidney Disease and the Cardiometabolic Syndrome, J. Clin. Hypert., 8(4): 546-48 (2006)). Conditions associated with kidney fibrosis include, but are not limited to, diabetic nephropathy, chronic kidney disease, end-stage renal disease, systemic lupus erythematosis, vasculitis, IgA nephropathy, other autoimmune diseases, paraprotein diseases, diabetes. Since chronic kidney disease associated with kidney fibrosis is a very important risk factor for cardiovascular disease, it would be apparent to a skilled artisan that a therapeutic that prevented or reduced kidney fibrosis would have a beneficial effect on cardiac and vascular disease throughout the body. A condition associated with kidney fibrosis, including kidney fibrosis itself can be diagnosed using methods known in the art, e.g., by a blood test that measures the level of waste products such as creatinine and urea, a urine test that looks for abnormalities, a test that measures the level of expression of SMOC2 gene or protein (see, e.g., WO2015/138532), an imaging test using ultrasound to assess kidney's structure and size, or a kidney biopsy.

In some embodiments, the disorder is chronic kidney disease. As used herein, "chronic kidney disease" or "CKD" refers to the progressive loss of kidney function over time. In some embodiments, CKD is characterized by hyperphosphatemia (i.e., >4.6 mg/dl) or low glomerular filtration rates (i.e., <90 ml/minute per 1.73 $m^2$ of body surface). However, many CKD patients may have normal serum phosphate levels in conjunction with a sustained reduction in glomerular filtration rate for 3 or more months, or a normal GFR in conjunction with sustained evidence of a structural abnormality of the kidney. In some embodiments, a subject with CKD can be a subject with either i) a sustained reduction in GFR <60 mi/min per 1.73 $m^2$ of body surface for 3 or more months; or ii) a structural or functional abnormality of renal function for 3 or more months even in the absence of a reduced GFR. Structural or anatomical abnormalities of the kidney could be defined as but not limited to persistent microalbuminuria or proteinuria or hematuria or presence of renal cysts.

Common symptoms of chronic kidney disease include tiredness, nausea, urine-like odor to the breath, bone pain, abnormally dark or light skin, itching, restless leg syndrome, blood in stools, bruising easily, pedal edema, and peripheral edema. Chronic kidney disease can be diagnosed through, e.g., medical history, a blood test that measures complete blood count, BUN level, or creatinine level, renal flow and scan, and renal ultrasound. In some embodiments, the subject is identified as having an elevated level of SMOC2, e.g., using a method described in WO2015138532, which is incorporated by reference herein in its entirety.

Generally, the methods include administering a therapeutically effective amount of an inhibitor of SMOC2 as described herein, to a subject who is in need of, or who has been determined to be in need of, such treatment. Inhibitors of SMOC2 include antibodies that bind to and inhibit SMOC2 as well as inhibitory nucleic acids targeting SMOC2 mRNA.

As used in this context, to "treat" means to ameliorate at least one symptom of the disorders associated with kidney fibrosis. Often, kidney fibrosis results in increased levels of BUN or creatinine, hyperphosphatemia and/or low glomerular filtration rates; thus, a treatment can result in a reduction in BUN, phosphate, or creatinine levels, and a return or approach to normal kidney function, e.g., glomerular filtration rates of at least 90 ml/minute per 1.73 $m^2$ of body surface. Administration of a therapeutically effective amount of a compound described herein for the treatment of a condition associated with kidney fibrosis will result in decreased fibrosis, detectable on ultrasound.

In some embodiments, the subjects treated using a method described herein do not have colon cancer, age-related macular degeneration, vitiligo, or pulmonary disease.

Antibodies

The methods described herein can include the use of antibodies to the Smoc2 protein. The term "antibody" as used herein refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments the antibody has effector function and can fix complement. In some embodiments, the antibody has reduced or no ability to bind an Fc receptor. For example, the antibody can be an isotype or subtype, fragment or other mutant, which does not support binding to an Fc receptor, e.g., it has a mutagenized or deleted Fc receptor binding region. Methods for making antibodies and fragments thereof are known in the art, see, e.g., Harlow et. al., editors, *Antibodies: A Laboratory Manual* (1988); Goding, *Monoclonal Antibodies: Principles and Practice*, (N.Y. Academic Press 1983); Howard and Kaser, *Making and Using Antibodies: A Practical Handbook* (CRC Press; 1st edition, Dec. 13, 2006); Kontermann and Dübel, *Antibody Engineering Volume 1 (Springer Protocols)* (Springer; 2nd ed., May 21, 2010); Lo, *Antibody Engineering: Methods and Protocols (Methods in Molecular Biology)* (Humana Press; Nov. 10, 2010); and Dübel, *Handbook of Therapeutic Antibodies: Technologies, Emerging Developments and Approved Therapeutics*, (Wiley-VCH; 1 edition Sep. 7, 2010). Antibodies useful in the present methods include those that bind specifically to (i.e., do not bind to targets other than) Smoc2, and inhibit fibroblast to myofibroblast activation.

In some embodiments, the antibody can be coupled to a detectable or imaging agent. Such agents are well known in the art and include paramagnetic agents, bioluminescent or fluorescent labels (e.g., GFP, FITC, rhodamine, or Texas Red), radioactive isotopes, and colorimetric/enzymatic agents (e.g., HRP, B-galactosidase). In a preferred embodiment, the antibody is coupled to a paramagnetic agent, e.g., a paramagnetic nanoparticle, e.g., cross-linked iron oxide (CLIO) nanoparticles; see, e.g., US 20110046004; Josephson et al., Bioconjug. Chem., 10(2):186-91 (1999).

Inhibitory Nucleic Acids

Inhibitory nucleic acids useful in the present methods and compositions include antisense oligonucleotides, ribozymes, external guide sequence (EGS) oligonucleotides, siRNA compounds, single- or double-stranded RNA interference (RNAi) compounds such as siRNA compounds, modified bases/locked nucleic acids (LNAs), peptide nucleic acids (PNAs), and other oligomeric compounds or oligonucleotide mimetics which hybridize to at least a portion of the target SMOC2 nucleic acid and modulate its function. In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof. See, e.g., WO 2010040112.

In some embodiments, the inhibitory nucleic acids are 10 to 50, 10 to 20, 10 to 25, 13 to 50, or 13 to 30 nucleotides in length. One having ordinary skill in the art will appreciate that this embodies inhibitory nucleic acids having complementary portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the inhibitory nucleic acids are 15 nucleotides in length. In some embodiments, the inhibitory nucleic acids are 12 or 13 to 20, 25, or 30 nucleotides in length. One having ordinary skill in the art will appreciate that this embodies inhibitory nucleic acids having complementary portions of 12, 13, 14, 15, 16, 17, 18, 19, 20, 21, 22, 23, 24, 25, 26, 27, 28, 29 or 30 nucleotides in length, or any range therewithin (complementary portions refers to those portions of the inhibitory nucleic acids that are complementary to the target sequence).

The inhibitory nucleic acids useful in the present methods are sufficiently complementary to the target RNA, i.e., hybridize sufficiently well and with sufficient specificity, to give the desired effect. "Complementary" refers to the capacity for pairing, through hydrogen bonding, between two sequences comprising naturally or non-naturally occurring bases or analogs thereof. For example, if a base at one position of an inhibitory nucleic acid is capable of hydrogen bonding with a base at the corresponding position of a RNA, then the bases are considered to be complementary to each other at that position. 100% complementarity is not required.

Routine methods can be used to design an inhibitory nucleic acid that binds to the SMOC2 sequence with sufficient specificity. In some embodiments, the methods include using bioinformatics methods known in the art to identify regions of secondary structure, e.g., one, two, or more stem-loop structures, or pseudoknots, and selecting those regions to target with an inhibitory nucleic acid. For example, "gene walk" methods can be used to optimize the inhibitory activity of the nucleic acid; for example, a series of oligonucleotides of 10-30 nucleotides spanning the length of a target RNA can be prepared, followed by testing for activity. Optionally, gaps, e.g., of 5-10 nucleotides or more, can be left between the target sequences to reduce the number of oligonucleotides synthesized and tested. GC content is preferably between about 30-60%. Contiguous runs of three or more Gs or Cs should be avoided where possible (for example, it may not be possible with very short (e.g., about 9-10 nt) oligonucleotides).

In some embodiments, the inhibitory nucleic acid molecules can be designed to target a specific region of the RNA sequence. For example, a specific functional region can be targeted, e.g., a region comprising a known RNA localization motif (i.e., a region complementary to the target nucleic acid on which the RNA acts). Alternatively, or in addition, highly conserved regions can be targeted, e.g., regions identified by aligning sequences from disparate species such as primate (e.g., human) and rodent (e.g., mouse) and looking for regions with high degrees of identity. Percent identity can be determined routinely using basic local alignment search tools (BLAST programs) (Altschul et al., J. Mol. Biol., 1990, 215, 403-410; Zhang and Madden, Genome Res., 1997, 7, 649-656), e.g., using the default parameters.

Once one or more target regions, segments or sites have been identified, e.g., within an SMOC2 sequence known in the art or provided herein, inhibitory nucleic acid compounds are chosen that are sufficiently complementary to the target, i.e., that hybridize sufficiently well and with sufficient specificity (i.e., do not substantially bind to other non-target RNAs), to give the desired effect.

In the context of this invention, hybridization means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as used herein, refers to the capacity for precise pairing between two nucleotides. For example, if a nucleotide at a certain position of an oligonucleotide is capable of hydrogen bonding with a nucleotide at the same position of a RNA molecule, then the inhibitory nucleic acid and the RNA are considered to be complementary to each other at that position. The inhibitory nucleic acids and the RNA are complementary to each other when a sufficient number of corresponding positions in each molecule are occupied by nucleotides which can hydrogen bond with each other. Thus, "specifically hybridisable" and "complementary" are terms which are used to indicate a sufficient degree of complementarity or precise pairing such that stable and specific binding occurs between the inhibitory nucleic acid and the RNA target. For example, if a base at one position of an inhibitory nucleic acid is capable of hydrogen bonding with a base at the corresponding position of a RNA, then the bases are considered to be complementary to each other at that position. 100% complementarity is not required.

It is understood in the art that a complementary nucleic acid sequence need not be 100% complementary to that of its target nucleic acid to be specifically hybridisable. A complementary nucleic acid sequence for purposes of the present methods is specifically hybridisable when binding of the sequence to the target RNA molecule interferes with the normal function of the target RNA to cause a loss of activity, and there is a sufficient degree of complementarity to avoid non-specific binding of the sequence to non-target RNA sequences under conditions in which specific binding is desired, e.g., under physiological conditions in the case of in vivo assays or therapeutic treatment, and in the case of in vitro assays, under conditions in which the assays are performed under suitable conditions of stringency. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., *Molecular Cloning: A Laboratory Manual*, Cold Spring Harbor Laboratory Press, New York.

In general, the inhibitory nucleic acids useful in the methods described herein have at least 80% sequence complementarity to a target region within the target nucleic acid, e.g., 90%, 95%, or 100% sequence complementarity to the target region within an RNA. For example, an antisense compound in which 18 of 20 nucleobases of the antisense oligonucleotide are complementary, and would therefore specifically hybridize, to a target region would represent 90 percent complementarity. Percent complementarity of an inhibitory nucleic acid with a region of a target nucleic acid can be determined routinely using basic local alignment search tools (BLAST programs) (Altschul et al., J. Mol. Biol., 1990, 215, 403-410; Zhang and Madden, Genome Res., 1997, 7, 649-656). Inhibitory nucleic acids that hybridize to an RNA can be identified through routine experimentation. In general, the inhibitory nucleic acids must retain specificity for their target, i.e., must not directly bind to, or directly significantly affect expression levels of, transcripts other than the intended target.

For further disclosure regarding inhibitory nucleic acids, please see US2010/0317718 (antisense oligos); US2010/0249052 (double-stranded ribonucleic acid (dsRNA));

US2009/0181914 and US2010/0234451 (LNAs); US2007/0191294 (siRNA analogues); US2008/0249039 (modified siRNA); and WO2010/129746 and WO2010/040112 (inhibitory nucleic acids).

Antisense

In some embodiments, the inhibitory nucleic acids are antisense oligonucleotides. Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to an RNA. Thus, oligonucleotides are chosen that are sufficiently complementary to the target, i.e., that hybridize sufficiently well and with sufficient specificity, to give the desired effect.

siRNA/shRNA

In some embodiments, the nucleic acid sequence that is complementary to an SMOC2 RNA can be an interfering RNA, including but not limited to a small interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In some embodiments, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al., Science 296:550-553, (2002); Lee et al, Nature Biotechnol., 20, 500-505, (2002); Miyagishi and Taira, Nature Biotechnol 20:497-500, (2002); Paddison et al. Genes & Dev. 16:948-958, (2002); Paul, Nature Biotechnol, 20, 505-508, (2002); Sui, Proc. Natl. Acad. Sd. USA, 99(6), 5515-5520, (2002); Yu et al. Proc Natl Acad Sci USA 99:6047-6052, (2002).

The target RNA cleavage reaction guided by siRNAs is highly sequence specific. In general, siRNA containing a nucleotide sequences identical to a portion of the target nucleic acid are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general, the siRNAs must retain specificity for their target, i.e., must not directly bind to, or directly significantly affect expression levels of, transcripts other than the intended target.

Ribozymes

Trans-cleaving enzymatic nucleic acid molecules can also be used; they have shown promise as therapeutic agents for human disease (Usman & McSwiggen, 1995 Ann. Rep. Med. Chem. 30, 285-294; Christoffersen and Marr, 1995 J. Med. Chem. 38, 2023-2037). Enzymatic nucleic acid molecules can be designed to cleave specific RNA targets within the background of cellular RNA. Such a cleavage event renders the RNA non-functional.

In general, enzymatic nucleic acids with RNA cleaving activity act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel, 1979, Proc. R. Soc. London, B 205, 435) have been used to evolve new nucleic acid catalysts capable of catalyzing a variety of reactions, such as cleavage and ligation of phosphodiester linkages and amide linkages, (Joyce, 1989, Gene, 82, 83-87; Beaudry et al., 1992, Science 257, 635-641; Joyce, 1992, Scientific American 267, 90-97; Breaker et al, 1994, TIBTECH 12, 268; Bartel et al, 1993, Science 261:1411-1418; Szostak, 1993, TIBS 17, 89-93; Kumar et al, 1995, FASEB J., 9, 1183; Breaker, 1996, Curr. Op. Biotech., 1, 442). The development of ribozymes that are optimal for catalytic activity would contribute significantly to any strategy that employs RNA-cleaving ribozymes for the purpose of regulating gene expression.

The hammerhead ribozyme, for example, functions with a catalytic rate (kcat) of about 1 $min^{-1}$ in the presence of saturating (10 mM) concentrations of $Mg^{2+}$ cofactor. An artificial "RNA ligase" ribozyme has been shown to catalyze the corresponding self-modification reaction with a rate of about 100 $min^{-1}$. In addition, it is known that certain modified hammerhead ribozymes that have substrate binding arms made of DNA catalyze RNA cleavage with multiple turn-over rates that approach 100 $min^{-1}$.

Modified Inhibitory Nucleic Acids

In some embodiments, the inhibitory nucleic acids used in the methods described herein are modified, e.g., comprise one or more modified bonds or bases. A number of modified bases include phosphorothioate, methylphosphonate, peptide nucleic acids, or locked nucleic acid (LNA) molecules. Some inhibitory nucleic acids are fully modified, while others are chimeric and contain two or more chemically distinct regions, each made up of at least one nucleotide. These inhibitory nucleic acids typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric inhibitory nucleic acids of the invention may be formed as composite structures of two or more oligonucleotides, modified oligonucleotides, oligonucleosides and/or oligonucleotide mimetics as described above. Such compounds have also been referred to in the art as hybrids or gapmers. In some embodiments, the oligonucleotide is a gapmer (contain a central stretch (gap) of DNA monomers sufficiently long to induce RNase H cleavage, flanked by blocks of LNA modified nucleotides; see, e.g., Stanton et al., Nucleic Acid Ther. 2012. 22: 344-359; Nowotny et al., Cell, 121:1005-1016, 2005; Kurreck, European Journal of Biochemistry 270:1628-1644, 2003; FLuiter et al., Mol Biosyst. 5(8):838-43, 2009). In some embodiments, the oligonucleotide is a mixmer (includes alternating short stretches of LNA and DNA; Naguibneva et al., Biomed Pharmacother. 2006 November; 60(9):633-8; from et al., Gene. 2006 May 10; 3720:137-41). Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, the inhibitory nucleic acid comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target.

A number of nucleotide and nucleoside modifications have been shown to make the oligonucleotide into which they are incorporated more resistant to nuclease digestion than the native oligodeoxynucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly CH2-NH—O—CH2, CH, ~N(CH3)~O~CH2 (known as a methylene(methylimino) or MMI backbone], CH2-O—N (CH3)-CH2, CH2-N(CH3)-N(CH3)-CH2 and O—N(CH3)-CH2-CH2 backbones, wherein the native phosphodiester backbone is represented as O—P—O—CH); amide backbones (see De Mesmaeker et al. Ace. Chem. Res. 1995, 28:366-374); morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050.

Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991.

Cyclohexenyl nucleic acid oligonucleotide mimetics are described in Wang et al., J. Am. Chem. Soc., 2000, 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264, 562; 5, 264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

One or more substituted sugar moieties can also be included, e.g., one of the following at the 2' position: OH, SH, $SCH_3$, F, OCN, $OCH_3OCH_3$, $OCH_3O(CH_2)n$ $CH_3$, O(CH$_2$)n NH$_2$ or O(CH$_2$)n CH$_3$ where n is from 1 to about 10; Ci to C10 lower alkyl, alkoxyalkoxy, substituted lower alkyl, alkaryl or aralkyl; Cl; Br; CN; CF3; OCF3; O-, S-, or N-alkyl; O-, S-, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-0-CH$_2$CH$_2$OCH$_3$, also known as 2'-O-(2-methoxyethyl)] (Martin et al, Helv. Chim. Acta, 1995, 78, 486). Other preferred modifications include 2'-methoxy (2'-O—CH3), 2'-propoxy (2'-OCH$_2$CH$_2$CH$_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Inhibitory nucleic acids can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalkylamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. Kornberg, A., DNA Replication, W. H. Freeman & Co., San Francisco, 1980, pp 75-77; Gebeyehu, G., et al. Nucl. Acids Res. 1987, 15:4513). A "universal" base known in the art, e.g., inosine, can also be included. 5-Me-C substitutions have been shown to increase nucleic acid duplex stability by 0.6-1.2<0>C. (Sanghvi, Y. S., in Crooke, S. T. and Lebleu, B., eds., Antisense Research and Applications, CRC Press, Boca Raton, 1993, pp. 276-278) and are presently preferred base substitutions.

It is not necessary for all positions in a given oligonucleotide to be uniformly modified, and in fact more than one of the aforementioned modifications may be incorporated in a single oligonucleotide or even at within a single nucleoside within an oligonucleotide.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500.

Inhibitory nucleic acids can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-O-methoxyethyl sugar modifications. Modified nucleobases are described in U.S. Pat. No. 3,687,808, as well as U.S. Pat. Nos. 4,845,205; 5,130, 302; 5,134,066; 5,175, 273; 5, 367,066; 5,432,272; 5,457, 187; 5,459,255; 5,484,908; 5,502,177; 5,525,711; 5,552, 540; 5,587,469; 5,596,091; 5,614,617; 5,750,692, and 5,681,941, each of which is herein incorporated by reference.

In some embodiments, the inhibitory nucleic acids are chemically linked to one or more moieties or conjugates that enhance the activity, cellular distribution, or cellular uptake of the oligonucleotide. Such moieties comprise but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al, Ann. N. Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxycholesterol moiety (Crooke et al., J. Pharmacol. Exp. Ther., 1996, 277, 923-937). See also U.S. Pat. Nos. 4,828,979; 4,948,882; 5,218,105; 5,525,465; 5,541,313; 5,545,730; 5,552, 538; 5,578,717, 5,580,731; 5,580,731; 5,591,584; 5,109,124; 5,118,802; 5,138,045; 5,414,077; 5,486, 603; 5,512,439; 5,578,718; 5,608,046; 4,587,044; 4,605,735; 4,667,025; 4,762, 779; 4,789,737; 4,824,941; 4,835,263; 4,876,335; 4,904,582; 4,958,013; 5,082, 830; 5,112,963; 5,214,136; 5,082,830; 5,112,963; 5,214,136; 5, 245,022; 5,254,469; 5,258,506; 5,262,536; 5,272,250; 5,292,873; 5,317,098; 5,371,241, 5,391, 723; 5,416,203, 5,451,463; 5,510,475; 5,512,667; 5,514,785; 5, 565,552; 5,567,810; 5,574,142; 5,585,481; 5,587,371; 5,595,726; 5,597,696; 5,599,923; 5,599, 928 and 5,688,941, each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Locked Nucleic Acids (LNAs)

In some embodiments, the modified inhibitory nucleic acids used in the methods described herein comprise locked nucleic acid (LNA) molecules, e.g., including [alpha]-L-LNAs. LNAs comprise ribonucleic acid analogues wherein the ribose ring is "locked" by a methylene bridge between the 2'-oxygen and the 4'-carbon—i.e., oligonucleotides containing at least one LNA monomer, that is, one 2'-O,4'-C-methylene-β-D-ribofuranosyl nucleotide. LNA bases form standard Watson-Crick base pairs but the locked configuration increases the rate and stability of the basepairing reaction (Jepsen et al., Oligonucleotides, 14, 130-146 (2004)). LNAs also have increased affinity to base pair with RNA as compared to DNA. These properties render LNAs especially useful as probes for fluorescence in situ hybridization (FISH) and comparative genomic hybridization, as knockdown tools for miRNAs, and as antisense oligonucleotides to target mRNAs or other RNAs, e.g., RNAs as described herein.

The LNA molecules can include molecules comprising 10-30, e.g., 12-24, e.g., 12, 13, 14, 15, 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the RNA. The LNA molecules can be chemically synthesized using methods known in the art.

The LNA molecules can be designed using any method known in the art; a number of algorithms are known, and are commercially available (e.g., on the internet, for example at exiqon.com). See, e.g., You et al., Nuc. Acids. Res. 34:e60 (2006); McTigue et al., Biochemistry 43:5388-405 (2004); and Levin et al., Nuc. Acids. Res. 34:e142 (2006). For example, "gene walk" methods, similar to those used to design antisense oligos, can be used to optimize the inhibitory activity of the LNA; for example, a series of oligonucleotides of 10-30 nucleotides spanning the length of a target RNA can be prepared, followed by testing for activity. Optionally, gaps, e.g., of 5-10 nucleotides or more, can be left between the LNAs to reduce the number of oligonucleotides synthesized and tested. GC content is preferably between about 30-60%. General guidelines for designing LNAs are known in the art; for example, LNA sequences will bind very tightly to other LNA sequences, so it is preferable to avoid significant complementarity within an LNA. Contiguous runs of more than four LNA residues, should be avoided where possible (for example, it may not be possible with very short (e.g., about 9-10 nt) oligonucleotides). In some embodiments, the LNAs are xylo-LNAs.

For additional information regarding LNAs see U.S. Pat. Nos. 6,268,490; 6,734,291; 6,770,748; 6,794,499; 7,034,133; 7,053,207; 7,060,809; 7,084,125; and 7,572,582; and U.S. Pre-Grant Pub. Nos. 20100267018; 20100261175; and 20100035968; Koshkin et al. Tetrahedron 54, 3607-3630 (1998); Obika et al. Tetrahedron Lett. 39, 5401-5404 (1998); Jepsen et al., Oligonucleotides 14:130-146 (2004); Kauppinen et al., Drug Disc. Today 2(3):287-290 (2005); and Ponting et al., Cell 136(4):629-641 (2009), and references cited therein.

Making and Using Inhibitory Nucleic Acids

The nucleic acid sequences used to practice the methods described herein, whether RNA, cDNA, genomic DNA, vectors, viruses or hybrids thereof, can be isolated from a variety of sources, genetically engineered, amplified, and/or expressed/generated recombinantly. Recombinant nucleic acid sequences can be individually isolated or cloned and tested for a desired activity. Any recombinant expression system can be used, including e.g. in vitro, bacterial, fungal, mammalian, yeast, insect or plant cell expression systems.

Nucleic acid sequences of the invention can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000)). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus. The recombinant vectors capable of expressing the nucleic acids of the invention can be delivered as described herein, and persist in target cells (e.g., stable transformants).

Nucleic acid sequences used to practice this invention can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Nucleic acid sequences of the invention can be stabilized against nucleolytic degradation such as by the incorporation of a modification, e.g., a nucleotide modification. For example, nucleic acid sequences of the invention can include a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom (see, e.g., Kaupinnen et al., Drug Disc. Today 2(3):287-290 (2005); Koshkin et al., J. Am. Chem. Soc., 120(50):13252-13253 (1998)). For additional modifications see US 20100004320, US 20090298916, and US 20090143326.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook et al., *Molecular Cloning; A Laboratory Manual* 3 d ed. (2001); *Current Protocols in Molecular Biology*, Ausubel et al., eds. (John Wiley & Sons, Inc., New York 2010); Kriegler, Gene *Transfer and Expression: A Laboratory Manual* (1990); *Laboratory Techniques In Biochemistry And Molecular Biology: Hybridization With Nucleic Acid Probes, Part I Theory and Nucleic Acid Preparation*, Tijssen, ed. Elsevier, N.Y. (1993).

Pharmaceutical Compositions

The methods described herein can include the administration of pharmaceutical compositions and formulations comprising inhibitory antibodies or nucleic acid sequences designed to target a SMOC2 RNA.

In some embodiments, the compositions are formulated with a pharmaceutically acceptable carrier. The pharmaceutical compositions and formulations can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., *Remington: The Science and Practice of Pharmacy*, 21st ed., 2005.

The inhibitory nucleic acids can be administered alone or as a component of a pharmaceutical formulation (composition). The compounds may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions of the invention include those suitable for intradermal, inhalation, oral/nasal, topical, parenteral, rectal, and/or intravaginal administration. The formulations may conveniently be presented in unit dosage form and may be prepared by any methods well known in the art of pharmacy. The amount of active ingredient (e.g., nucleic acid sequences of this invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g., an antigen specific T cell or humoral response.

Pharmaceutical formulations can be prepared according to any method known to the art for the manufacture of pharmaceuticals. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., nucleic acid sequences of the invention) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

In some embodiments, oil-based pharmaceuticals are used for administration of nucleic acid sequences of the invention. Oil-based suspensions can be formulated by suspending an active agent in a vegetable oil, such as *arachis* oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an anti-oxidant such as ascorbic acid. As an example of an injectable oil vehicle, see Minto (1997) J. Pharmacol. Exp. Ther. 281:93-102.

Pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions of the invention comprise a paraffin oil, a sorbitan monooleate, an ethoxylated sorbitan monooleate and/or an ethoxylated sorbitan trioleate.

The pharmaceutical compounds can also be administered by in intranasal, intraocular and intravaginal routes including suppositories, insufflation, powders and aerosol formulations (for examples of steroid inhalants, see e.g., Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In some embodiments, the pharmaceutical compounds can be delivered transdermally, by a topical route, formulated as applicator sticks, solutions, suspensions, emulsions, gels, creams, ointments, pastes, jellies, paints, powders, and aerosols.

In some embodiments, the pharmaceutical compounds can also be delivered as microspheres for slow release in the body. For example, microspheres can be administered via intradermal injection of drug which slowly release subcutaneously; see Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In some embodiments, the pharmaceutical compounds can be parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose, any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

In some embodiments, the pharmaceutical compounds and formulations can be lyophilized. Stable lyophilized formulations comprising an inhibitory nucleic acid can be made by lyophilizing a solution comprising a pharmaceutical of the invention and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. 20040028670.

The compositions and formulations can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587. As used in the present invention, the term "liposome" means a vesicle composed of amphiphilic lipids arranged in a bilayer or bilayers. Liposomes are unilamellar or multilamellar vesicles that have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes can also include "sterically stabilized" liposomes, i.e., liposomes comprising one or more specialized lipids. When incorporated into liposomes, these specialized lipids result in liposomes with enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The formulations of the invention can be administered for prophylactic and/or therapeutic treatments. In some embodiments, for therapeutic applications, compositions are administered to a subject who is need of reduced triglyceride levels, or who is at risk of or has a disorder described herein, in an amount sufficient to cure, alleviate or partially arrest the clinical manifestations of the disorder or its complications; this can be called a therapeutically effective amount. For example, in some embodiments, pharmaceutical compositions of the invention are administered in an amount sufficient to decrease serum levels of triglycerides in the subject.

The amount of pharmaceutical composition adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; *Remington: The Science and Practice of Pharmacy,* 21st ed., 2005). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on for example: the dosage and frequency as required and tolerated by the patient, the degree and amount of therapeutic effect generated after each administration (e.g., effect on tumor size or growth), and the like. The formulations should provide a sufficient quantity of active agent to effectively treat, prevent or ameliorate conditions, diseases or symptoms.

In alternative embodiments, pharmaceutical formulations for oral administration are in a daily amount of between about 1 to 100 or more mg per kilogram of body weight per day. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as *Remington: The Science and Practice of Pharmacy,* 21st ed., 2005.

Various studies have reported successful mammalian dosing using complementary nucleic acid sequences. See, for example, Esau C., et al., (2006) Cell Metabolism, 3(2):87-98; Krützfeldt J., et al., (2005) Nature 438, 685-689; Elmen J., et al., (2008) Nature 452, 896-899.

Combination Treatments

The methods described herein can include the use of standard treatments in addition to the inhibitor of SMOC2. Treatments for kidney fibrosis and/or chronic kidney disease are known in the art and include, by way of non-limiting example, dialysis; transplant; low protein diet; an ACE inhibitor (e.g. perindopril, captopril, enalapril, lisinopril, or ramipril); an angiotensin II receptor blocker (ARB) (e.g., Losartan, irbesartan, olmesartan, candesartan, valsartan, fimasartan, or telmisartan); lipid control (e.g., statins); D-vitamin supplementation; phosphate control; anemia control (e.g., erythroid stimulating agents); acidosis prevention (e.g., sodium bicarbonate); and uric acid control (e.g., allopurinol).

EXAMPLES

The invention is further described in the following examples, which do not limit the scope of the invention described in the claims.

Methods

The following materials and methods were used in the following examples.

Human Studies

The Institutional Review Board approved the protocols for recruitment and urine sample collection, which was performed with written informed consent of the participants. Urine samples from patients with Chronic Kidney Disease (CKD) were obtained from the Brigham and Women's Hospital (BWH) ambulatory nephrology clinic. For this study we included patients with stage 4 or 5 CKD (estimated glomerular filtration rate (eGFR)<30 ml/min/1.73 m$^2$). Patients were excluded if they had a recent hospitalization or episode of AKI (>50% rise in serum creatinine over a 1-week period) within 3 months, or reported or suspected urinary tract infection within the past 3 weeks. Urine samples from healthy volunteers were obtained from the PhenoGenetics Project, a study of the impact of genetic variation in healthy individuals. Participants 19 to 75 years of age were recruited from the Boston area through advertisements in local media and flyers. The Inclusion criterion was a willingness to provide 120 mL of blood four times per year for five years. Exclusion criteria were the presence of self-reported inflammatory diseases (e.g., asthma or psoriasis), autoimmune diseases (e.g, lupus of multiple sclerosis), chronic metabolic diseases (e.g, thyroid disease or diabetes), or chronic infections (e.g., Hepatitis B or C; HIV). Urine was collected, centrifuged at 3200G for 5 min, and the supernatants collected and stored at −80 C within 4 hours of collection. De-identified human kidney tissue samples from patients with or without severe kidney fibrosis (n=10) were obtained from the Department of Pathology at Brigham and Women's Hospital.

Animal Studies

Genetic Mouse Models:

SMOC2 Overexpressing Transgenic (Tg (Smoc2-EGFP) HY194Gsat/Mmucd) (SMOC2 Tg) mice were purchased by the University of California, and generated using a modified BAC, containing an inserted EGFP upstream of targeted SMOC2 gene, that was injected into pronuclei of FVB/N fertilized oocytes. Hemizygous progeny was mated to IcrTac:ICR mice each generation thereafter. Smoc2$^{tm1.1\ (KOMP)}$ $_{Vlcg}$ was generated by the Knockout Mouse Phenotyping Program (KOMP$^2$) at The Jackson Laboratory using embryonic stem cells provided by the International Knockout Mouse Consortium. The ZEN-UB1 Velocigene cassette was inserted into the gene replacing all coding exons and intervening sequences. The construct was introduced into C57BL/6N-derived VGB6 embryonic stem (ES) cells, and correctly targeted ES cells were injected into B6 (Cg)-Tyrc-2J/J (Stock No. 58) blastocysts. The resulting chimeric males were bred to C57BL/6J females and then to B6N.Cg-Tg (Sox2-cre)1Amc/J (Stock No. 014094) to remove neo cassette. Resulting offspring were crossed to remove the cre-expressing transgene. Genotyping was performed using appropriate primers (Table 1). Genetic mouse models were compared to their respective Wild type littermates. All C57BL/6J mice used for experimentation were purchased from Charles River Laboratories. All animal maintenance and treatment protocols were in compliance with the Guide for Care and Use of Laboratory Animals as adopted and promulgated by the National Institutes of Health and were approved by the Harvard Medical School Animal Care and Use Committees.

TABLE 1

List of primers used for Genotyping

| Gene | F/R | Sequence | SEQ ID NO: |
|---|---|---|---|
| Wild type | F | TCC TTC TCC AGC ACC AAG TC | 1 |
| | R | TGA TCC AAA AGT GCC TCC TC | 2 |
| KO | F | CGG TCG CTA CCA TTA CCA GT | 3 |
| | R | CAT GCT CTG AGA AAT AAT TAC CAA | 4 |
| Transgenic | F | TGA CAG CAG CAG CGG CAG TT | 5 |
| | R | TAG CGG CTG AAG CAC TGC A | 6 |

Experimental Models of Fibrosis:

Mouse models of kidney fibrosis were used as previously described in detail by our group (29). The following models are briefly described:

Folic Acid (FA) Model.

Under the same housing/diet conditions, male SMOC2 Tg with their matched strain control (FVB/N and IcrTac:ICR) (25-29 g), male SMOC2 KO mice with their strain-matched control (C57BL/6) (21-24 g), and male BALB/c mice (25-29 g) aged 8 to 12 weeks received a single intraperitoneal (ip) injection of 250 mg/kg FA dissolved in a 0.3 M sodium bicarbonate solution (29). Mice were euthanized at 7 and 14 days following administration. Euthanasia was performed under isoflurane anesthesia.

Unilateral Ureter Obstruction (UUO) Model.

Female SMOC2 Tg mice with their matched strain control (FVB/N and IcrTac:ICR) (25-29 g), and male BALB/c mice (25-29 g) aged 8 to 12 weeks were anesthetized (50 mg/kg pentobarbital sodium, ip), and their left kidney was exposed by flank incision. The ureter was ligated at 2 points proximal to the kidney with 6-0 sutures. Sham mice had kidney exposed but their ureter was not tied. Contralateral Kidney (CoK) tissue was isolated from 14-day post-UUO treatment of SMOC2 Tg and Wild type. Mice received fluid lost replacement (1 mL normal saline, heated at 37° C., subcutaneously) immediately after surgery. The animals were sacrificed at 7 and 14 days following surgery. Euthanasia was performed under isoflurane anesthesia.

siRNA Administration.

Male C57BL/6 mice (21-24 g) aged 8 weeks received siRNA SMOC2 (30 μg/200 μL) or control scrambled siRNA (30 μg/200 μL) in RNAse-free phosphate-buffered saline (PBS) carriage medium by intravenous injection at −4 h, +2 d, +4 d, and +6 d from folic acid/vehicle treatment.

Pathology and Immunostainings

Whole Body Pathology:

Whole mouse necropsy was performed on male and female mice (n=6/each) of all 4 groups (SMOC2-KO, SMOC2-Tg, and their respective littermate controls) to investigate pathological differences between the groups. Organs were formalin-fixed, dehydrated in 70% EtOH, paraffin-embedded and H&E stained. The Dana-Farber/Harvard Cancer Center pathology core led by Dr. Peter Howley provided a detailed certified report for histological analysis of all organs.

Histology and Staining's:

For histologic evaluation, kidney tissues were perfused with cold PBS before harvesting. Samples for immunofluorescence were fixed in 4% paraformaldehyde at 4° C. for 24 h, then washed in 30% sucrose solution overnight prior to cryopreservation in Tissue-Tek O.C.T. (VWR, Radnor, Pa.). Samples for histological staining were fixed in formalin for 24 hours and then stored in 70% ethanol before being embedded in paraffin. Human kidney samples were received embedded in paraffin. Paraffin-embedded tissues were cut into 4- to 6-µm sections and stained with Masson's Trichrome and Picrosirius Red. Images were captured on a Carl Zeiss AxioImager.M2 using AxioVision SE64 software by Plan Apochromat 20x/0.8 objective. All images were analyzed through NIH ImageJ using a color threshold algorithm (identical threshold settings for compared image sets) written by G. Landini (version v1.8) available at dentistry.bham.ac.uk/landinig/software/software.html.

Immunofluorescence and Quantitative Microscopy:

OCT embedded mouse kidneys and paraffin embedded human kidneys were cut into 4- to 6-µm sections and permeabilized in 1×PBS containing Triton X-100 (0.1%) for 10 minutes. The sections were then labeled with Cy3-αSMA (1:500; Cell Signaling, C6198), αSMA-FITC (1:500; Sigma-Aldrich, F3777) and anti-SMOC2 (1/250; Santa Cruz Biotechnology, SC-67396). Slides with anti-SMOC2 were subsequently exposed to Donkey Anti-Rabbit specific Cy3-conjugated secondary antibodies (1:500; Jackson ImmunoResearch Laboratories, 711-165-152). 4,6-Diamidino-2-phenylindole (Sigma-Aldrich) was used for nuclear staining (blue). Confocal images were acquired in the Nikon Imaging Center at Harvard Medical School. Images were collected with a Yokogawa CSU-X1 spinning disk confocal with Borealis modification, mounted on a Nikon Ti inverted microscope equipped with 20x/0.75 Plan Apo, 40x/1.3 Plan Fluor, 60x/1.4 Plan Apo objective lens, a Prior Proscan II motorized stage and the Nikon Perfect Focus System for continuous maintenance of focus. FITC fluorescence was excited with an AOTF-controlled 488 nm solid state laser and collected with a 525/50 emission filter (Chroma). Cy3 fluorescence was excited with an AOTF-controlled 561 nm solid-state laser and collected with a 620/60 emission filter (Chroma). For both FITC and Cy3, a Quad 405/491/561/642 dichroic mirror was used (Semrock). DAPI was excited using a Lumencor SOLA with a 395/25 excitation filter, and emission was collected through the spinning disc head using a 460/25 emission filter. Images were acquired with a Hamamatsu ORCAAG cooled CCD camera controlled with MetaMorph 7 software. Brightness and contrast were adjusted on displayed images (identically for compared image sets) and quantified (identical threshold settings for compared image sets) using MetaMorph 7 software.

Western Blot Analysis

Kidney tissues and cell cultures were homogenized in RIPA buffer (ThermoFisher Scientific, 50 mM Tris-HCl [pH 7.4], 150 mM NaCl, 1% NP40) containing 1× protease and phosphatase inhibitor cocktail (Roche Applied Science). Protein concentrations were determined using the BCA protein estimation kit (Pierce) and an equal amount of protein (25 µg) was loaded on either a 10% or 12% polyacrylamide gel (PAGE). Protein transfer was performed using a nitrocellulose membrane. The following primary antibodies were used to detect the specific protein: anti-SMOC2 (1/250; Santa Cruz Biotechnology, SC-67396), anti-αSMA (1/1000; Sigma-Aldrich, A2547), anti-Collagen 1α1 (1:250; Novus, NB600-408), anti-Fibronectin (1:250; Abcam, ab23750), anti-GAPDH (1/5000; Abcam, ab181602), anti-Phospho-Myosin Light Chain 2 (Thr18/Ser19) (1/1000; Cell Signaling, #3674), anti-Phospho-Paxillin (Tyr118) (1/1000; Cell Signaling, #2541), Anti-Phospho-FAK (Tyr925) (1/1000; Cell Signaling, #3284). Horseradish peroxidase-conjugated secondary antibodies against mouse (Cell Signaling, #7076) and rabbit (Cell Signaling, #7074) were used to detect the appropriate primary antibody. Bands were detected with enhanced chemiluminescence (ECL) method (Pierce) and captured with Gel Doc™ XR+System (BioRad).

Quantitative Real-Time PCR

Total RNA was isolated from cell cultures or tissue samples using TRIzol (Invitrogen, Grand Island, N.Y.) according to the manufacturer's protocol. RNA concentration was measured using a NanoDrop spectrophotometer (ThermoFisher Scientific, Wilmington, Del.). Isolated RNA (1ug) was reverse transcribed into cDNA using a QuantiTect Reverse Transcription kit from Qiagen (Valencia, Calif.). Quantitative real-time PCR was performed using a QuantiFast SYBR Green PCR kit (Qiagen) on a QuantStudio7 (Applied Biosystems by Life Technologies) with the following thermal profile: activation 15 s at 95° C.; 40 cycles of annealing/elongation 15 s at 94° C., 30 s at 60° C.; extension 30 s at 72° C. All samples were measured with technical duplicates and normalized against GAPDH. Changes in the mRNA expression were calculated using the ΔΔCt method relative to a control. Forward and reverse primer sequences for mouse-specific genes are listed in Table 2.

TABLE 2

List of primers used for qRT-PCR

| Gene | F/R | Sequence | SEQ ID NO: |
|---|---|---|---|
| αSMA | F | GTC CCA GAC ATC AGG GAG TAA | 7 |
|  | R | TCG GAT ACT TCA GCG TCA GGA | 8 |
| Fibronectin | F | ATG TGG ACC CCT CCT GAT AGT | 9 |
|  | R | GCC CAG TGA TTT CAG CAA AGG | 10 |
| Smoc2 | F | CCG TAC AAG AAC TGA TGG GC | 11 |
|  | R | CTT TCA GCA TGA CCT CTG GG | 12 |
| Col1a1 | F | TGA CTG GAA GAG CGG AGA GT | 13 |
|  | R | GTT CGG GCT GAT GTA CCA GT | 14 |
| GAPDH | F | ATT GCC CTC AAC GAC CAC TTT G | 15 |
|  | R | TCT CTC TTC CTC TTG TGC TCT TGC | 16 |

RNA Sequencing

Library Preparation:

RNA samples (n=3-4 mice/timepoint/group) were checked for quality and quantity using nanodrop and Agilent Bioanalyzer instrument. All RNA samples had RIN numbers higher than 7. Libraries were prepared using a TruSeq Stranded mRNA Library Prep Kit (Illumina) following the manufacturer's protocol modified as follows: For each sample 330 ng of RNA was input with 6.67 ul of 1:1000 ERCC spike-in Mix 2 (Ambion), fragmentation was done for 8 minutes, and 13 PCR cycles was used for the final library amplification. The finished dsDNA libraries were quantified by Qubit fluorometer, Agilent TapeStation 2200, and RT-qPCR using the Kapa Biosystems library quantification kit according to manufacturer's protocols. Uniquely indexed libraries were pooled in equimolar ratios and sequenced on a single Illumina NextSeq500 run with single-end 75 bp reads by the Dana-Farber Cancer Institute Molecular Biology Core Facilities. STAR aligner was used to map sequenced reads to the mm9 genome assembly and to quantify gene level expression. The full dataset is available in the NCBI GEO database with the accession number GSE85209.

Bioinformatics Analysis:

All samples were processed using an RNA-seq pipeline implemented in the bcbio-nextgen project (https://bcbio-nextgen.readthedocs.org/en/latest/). Raw reads were examined for quality issues using FastQC (http://www.bioinformatics.babraham.ac.uk/projects/fastqc/) to ensure library generation and sequencing were suitable for further analysis. Adapter sequences, other contaminant sequences such as polyA tails and low-quality sequences with PHRED quality scores less than five were trimmed from reads using cutadapt (30). Trimmed reads were aligned to UCSC build 10 of the *Mus musculus* genome (mm10), augmented with transcript information from Ensembl release GRCm38 using the STAR aligner (31). Alignments were checked for evenness of coverage, rRNA content, genomic context of alignments (for example, alignments in known transcripts and introns), complexity and other quality checks using a combination of FastQC, Qualimap (32) and custom scripts. Counts of reads aligning to known genes were generated by featureCounts (33). Differential expression at the gene level was called with DESeq2 (34). DESeq2 was used to find how the two genotypes reacted differently to treatment using the Wald significance test and formula designed to find the "difference in differences", or the intersection term between genotype and treatment in this DESeq2 design formula: genotype+Treatment+genotype:Treatment. As a result of this approach, fold-change values describe the differential effect of genotype on expression changes after treatment, not the direct gene expression which would be observed directly between two sample classes. PCA analysis was performed on DESeq2 normalized, rlog variance stabilized reads. A cut-off-free gene set enrichment analysis (GSEA) for gene ontology (GO) and KEGG terms was performed on the fold change values derived from DESeq2 using GAGE (35) and visualized with REVIGO (36) treemaps. Expression patterns of genes within enriched enriched GO terms were visualized by heatmap, after centering and scaling each genotype's expression values to their respective untreated samples mean expression values (i.e. each sample's expression value was subtracted from the mean expression value for the sample genotype's untreated samples and divided by the mean's associated standard deviation).

Cell Culture, Reagents and In Vitro Assays

In Vitro Cell Culture:

NIH3T3 cells were purchased from ATCC and grown as a monolayer in polystyrene culture dishes containing Dulbecco's Modified Eagle Medium: Nutrient Mixture F-12 (DMEM/F12) (Invitrogen Corporation) supplemented with 10% FBS (Invitrogen Corporation). Cells were grown until 80% confluency before passage. HPTECs were purchased from Biopredic (Paris, France) and cultured in DMEM/F12 supplemented with hydrocortisone, EGF, insulin, transferrin, and sodium selenite. Cells were maintained at 37° C. in a humidified 5% $CO_2$ incubator. For experiments studying fibroblast-to-myofibroblast transition (37), fibroblasts were cultured in DMEM/F12 10% FBS at low density for 24 h, then at 40-50% confluency changed media to DMEM/F12 1% FBS for 4 h prior to treatments with SMOC2 (Preprotech) and/or TGFβ1 (Preprotech). Cell lines were not reported in the ICLAC database of commonly misidentified cell lines.

Transfections:

For SMOC2 knockdown experiments, NIH3T3 fibroblasts were transfected with 100 nM scramble or SMOC2 siRNA (Dharmacon, Lafayette, Colo.) with siPORT NeoFX transfection reagent (Life Technologies, Grand Island, N.Y.) following the manufacturer's protocol. After 24 hrs in DMEM/F12 10% FBS, cells were harvested for Western blot analysis or were treated with trypsin and reseeded at 40% confluency in cases of TGFβ1 stimulation. For SMOC2 overexpression, NIH3T3 cells were transfected with either pCMV Myc (pCMV) or SMOC2 (Myc-DDK-tagged)-Human SPARC (pCMV-SMOC2) plasmids (Origene Technologies, Rockville, Md.) with Lipofectamine 2000 (Life Technologies, Grand Island, N.Y.) following the manufacturer's protocol. After 24 hrs in DMEM/F12 10% FBS, cells were harvested for Western blot and RT-PCR analysis or were treated with trypsin and reseeded at 40% confluency for various assays.

Immunofluorescence:

NIH3T3 cells were fixed with 4% paraformaldehyde (Fisher) in PBS, permeabilized with 0.1% Triton X-100 (Fisher) in PBS, then blocked in 3% bovine-serum albumin (Sigma). Cytoskeletal F-Actin was visualized using Alexa Fluor 564-conjugated Rhodamine Phalloidin (Thermo) at 1:500 in PBS for 1 h. 4,6-Diamidino-2-phenylindole (Sigma-Aldrich) was used for nuclear staining (blue). Confocal images were acquired in the Nikon Imaging Center at Harvard Medical School as described above.

Scratch Assay:

Fibroblasts were grown to a semi-confluent monolayer, then in DMEM/F12 1% FBS were mechanically scratched (wound) using a standard 200ł, pipette tip. Suspension cells were washed away with DMEM/F12 1% FBS. Along the scratch, pre-fixed points were selected for representative photographs at 0 h and 24 h after initialization of the wound using a phase-contrast microscope. Wound closure was calculated by the percentage of newly area covered of SMOC2-treated fibroblasts over normal during 24 h (n=5, 3 images per sample). Distance migrated from untreated cells was taken as 100%. Representative images have been stained with methylene blue at 24 h for increased contrast.

MTT Assay:

Seven thousand and five hundred NIH3T3 cells were plated in a 96-well plate for 24 h, after which they were serum deprived in DMEM/F12 0.5% FBS. Fibroblasts then treated with different concentration of SMOC2 for 24, 48, 72 and 96 h in 0.2% FBS. To each sample, 1 mg/ml MTT was added 2 h prior to each time point. The medium was aspirated, and 100 ml isopropanol was added. Absorbance was measured at 570 nm taking 630 nm as a reference using SpectraMax Paradigm (Molecular Devices, Sunnyvale, Calif.). Absorbance obtained from untreated cells was taken as 100% (n=5 per concentration per time point).

Boyden Chamber Assay:

Serum free media in the presence and absence of treatments were added in the lower chamber of a Chemotaxis Cell Migration Assay, 96-well (8 μm) plate (Millipore). NIH3T3 cells were grown in 10% FBS for 24 h before being plated in 0.2% FBS of the upper migration chamber of a 8 μM 96-well plate for 24 h. The migration assay was performed following the manufacturer's protocol.

Cell Adhesion Assay:

Seven thousand and five hundred NIH3T3 cells were plated in a 96-well plate for 24 h. Cells were harvested with trypsin and reseeded into 96-well plates at 37° C. After 1 h incubation, unattached cells were removed by 2×PBS washes. Adherent fibroblasts were fixed with methanol and stained with 1% crystal violet. Absorbance was measured using SpectraMax Paradigm (Molecular Devices, Sunnyvale, Calif.). Absorbance obtained from untreated cells was taken as 100% (n=3).

Statistical Analysis

Data are expressed as the average±standard error. Statistical significance for multiple comparisons was evaluated by one-way analysis of variance (ANOVA) with Tukey post-hoc analysis (P<0.05), using GraphPad Prism (GraphPad software). Statistical significance for single comparisons was calculated by two-tailed Student's t-test (P<0.05), using Microsoft Excel (Microsoft Corporation). The sample size was predetermined based on the effect size and variability observed previously from similar readouts in our laboratory.

Example 1. SMOC2 is Highly Induced in Mice and Human Kidneys Following Fibrosis

Figure 1A:
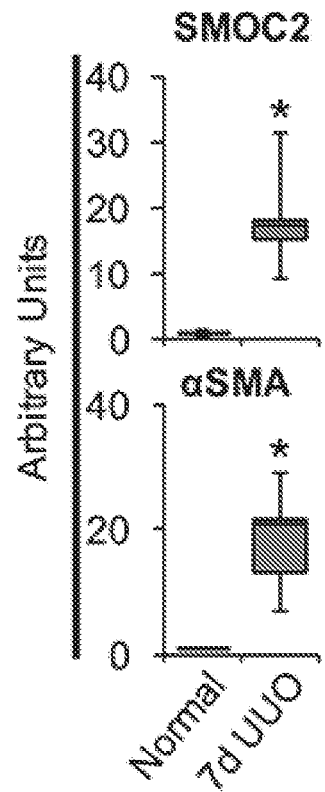
FIGS. 1A-F. SMOC2 is highly unregulated in mice and humans with kidney fibrosis. Quantitative immunostaining for SMOC2 and aSMA was performed on kidney sections obtained from mice at day 7 following (A) Unilateral Ureteral Obstruction (UUO) or (B) Folic acid injection (FA) (n=5; 20× magnification). For the UUO model, Contralateral Kidney (CoK) tissue from day 14 was also included. Relative quantitation of SMOC2 and αSMA immunofluorescence, as represented in a box plot, was performed using representative images of 5 visual fields for each tissue analyzed. (C, D) Representative Western blot (n=5/condition; Densitometry FIGS. 7C (UUO) and 7D (FA)) of SMOC2, αSMA, collagen 1α1 and fibronectin expression using kidney samples obtained from mice subjected to 7 and 14 days of UUO or FA. (E) Quantitative immunostaining for SMOC2 and αSMA in human kidneys with pathological fibrosis underlying Chronic Kidney Disease (CKD) (n=5) and non-fibrotic patients (n=5). Relative quantitation of SMOC2 and αSMA immunofluorescence as represented in a box plot was performed using representative images of 5 visual fields for each tissue analyzed. (F) Urinary levels of SMOC2 and Kidney Injury Molecule-1 (KIM-1) normalized to urinary creatinine were measured in patients with CKD (n=13) compared to healthy volunteers (n=13). Box plots describe the median (line within box), upper and lower quartiles (bounds of box), and minimum and maximum values (bars). *$P<0.05$ determined by t-test. Yellow arrows, tubules. White arrows, interstitium.
Figure 1B:
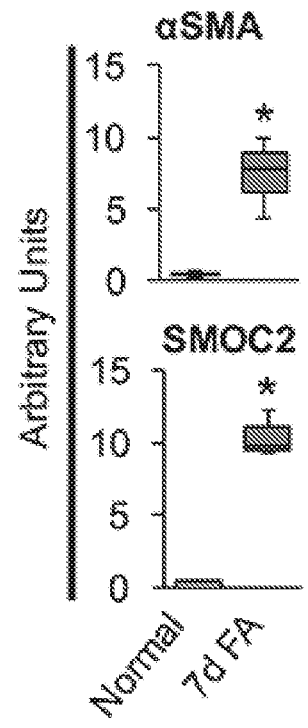
Figure 1C:
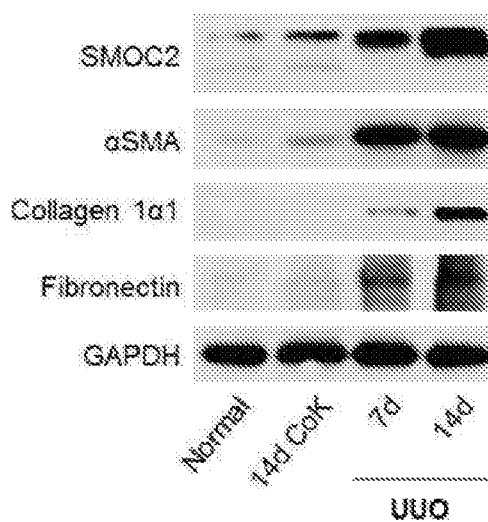
Figure 1D:
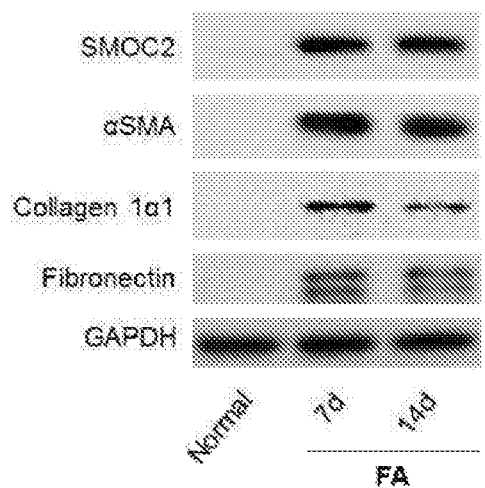
Figure 1E:
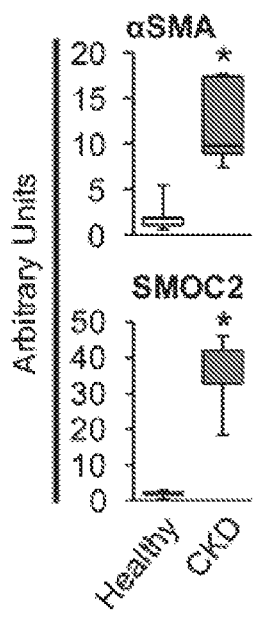
Figure 1F:
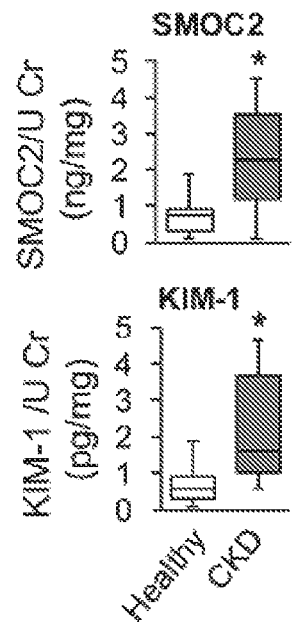
Figure 7A:
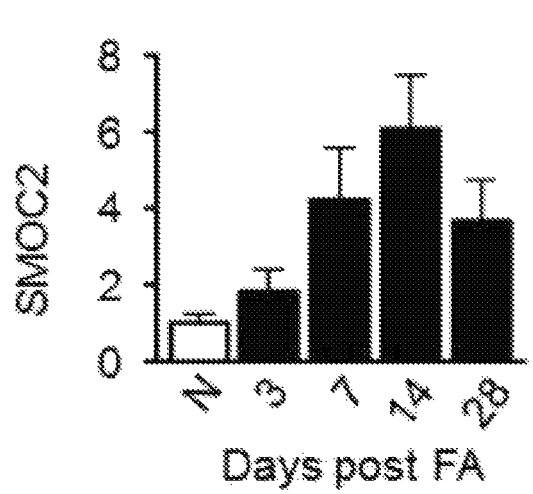
Figure 7B:
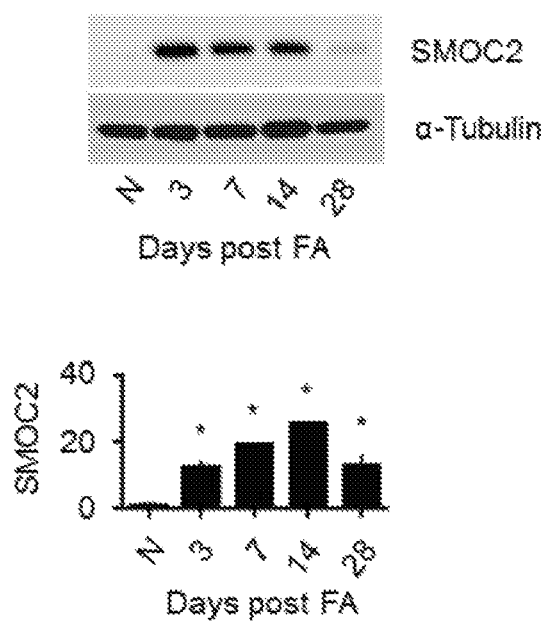
Figure 7C:
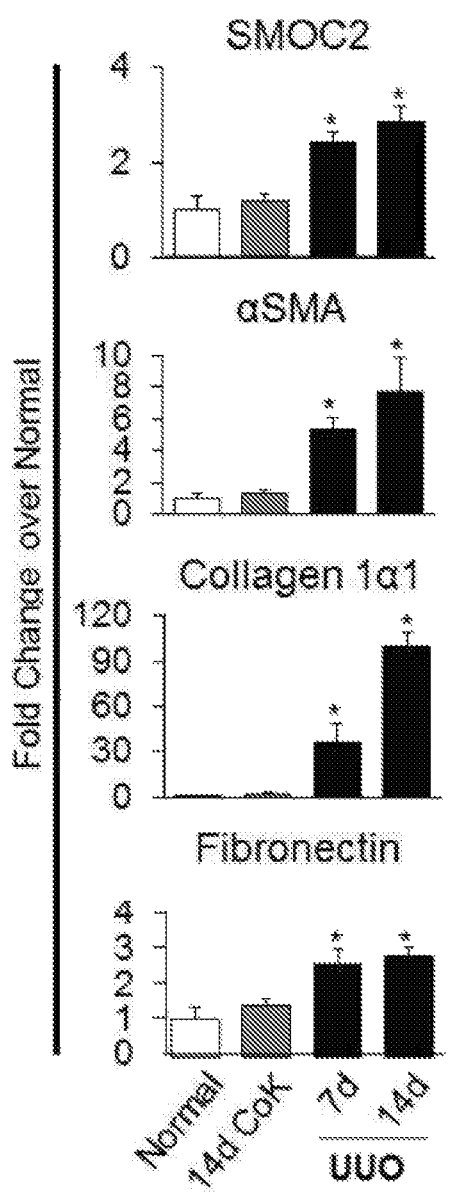
Figure 7D:
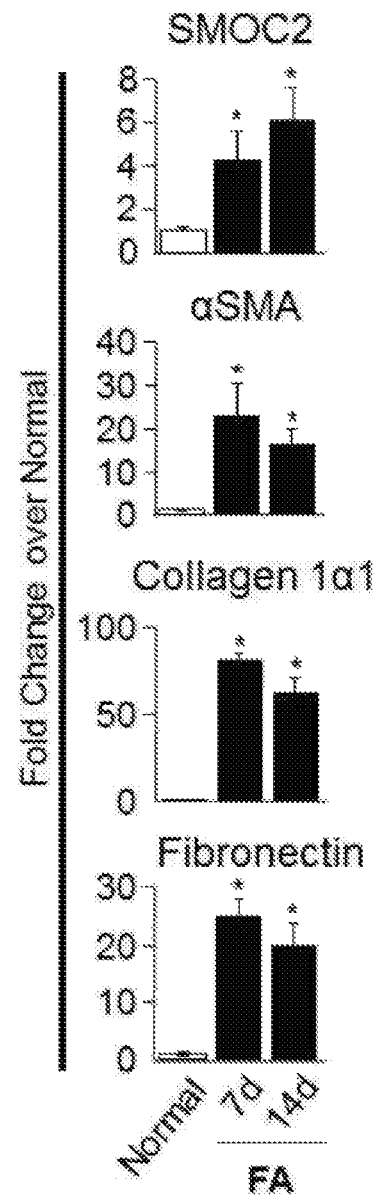

SMOC2 was significantly (P<0.05) induced in mice subjected to Unilateral Ureteral Obstruction (UUO) or treated with Folic acid (FA, 250 mg/kg ip), two mechanistically distinct mouse models of kidney injury with resulting progressive fibrosis (FIGS. 1A-D, 7A and B) (UUO Craciun et al., J Am Soc Nephrol. 2016; 27(6):1702-13; Craciun et al., Am J Physiol Renal Physiol. 2014; 307(4):F471-84; Yuan et al., Am J Pathol. 2003; 163(6):2289-301; Long et al., J Am Soc Nephrol. 2001; 12(12):2721-31; Surendran et al., Kidney Int. 2004; 65(6):2212-22; Kang et al., Nat Med. 2015; 21(1):37-46; Kang et al., Cell Rep. 2016; 14(4):861-71; Chevalier et al., Kidney Int. 2009; 75(11):1145-52; Yang et al., Nat Med. 2010; 16(5):535-43, 1p following 143). Co-staining of SMOC2 with αSMA in the kidneys of mice subjected to UUO or FA at 7 days confirmed the widespread upregulation of SMOC2 throughout the kidney, predominantly in the proximal and distal tubular epithelial cells around the areas of fibrosis (FIGS. 1A and 1B). In relation to αSMA (FIG. 1A, bottom panel), SMOC2 did not co-localize with myofibroblasts rather it was expressed around the myofibroblasts that are the effector cells of fibrosis, complying with the extracellular expression of SMOC2. In both UUO and FA models, SMOC2 expression correlated with progression of fibrosis characterized by the expression of +αSMA-myofibroblasts, collagen, and fibronectin (FIGS. 1C and 1D, densitometry FIGS. 7C and D). Previously, we have extended the histological effects of folic acid on renal function (Craciun et al., J Am Soc Nephrol. 2016; 27(6): 1702-13), in which FA induced tubulointerstitial fibrosis (histological analysis and fibrotic marker expression) correlated with a decline in renal function. Translatability of SMOC2 expression in human disease was confirmed by observing a significant induction of SMOC2 in the tubular epithelial cells of human kidney biopsy sections from patients with pathological fibrosis (FIG. 1E and FIG. 7C). SMOC2 being a secreted protein was also significantly elevated (2.5 fold, p<0.05) in the urine of patients with chronic kidney disease (CKD, Table 3, n=13) as compared to healthy volunteers (n=13). This increase corresponded with the increase in tubular damage biomarker Kidney Injury Molecule-1 (FIG. 1F). Consistent with these in vivo findings, SMOC2 expression was also significantly increased in mouse embryonic fibroblasts (NIH3T3) and in primary human proximal tubular epithelial cells (HPTECs) upon treatment with the profibrotic cytokine TGFβ1 (10 ng/ml) (FIGS. 8A-B).

TABLE 3

Demographics and clinical characteristics of patients with or without chronic kidney disease (CKD).

| Participant | Age | Sex | Race | eGFR (ml/min/1.73 m$^2$) | Stage | Cause of CKD | SMOC2/ U Cr (ng/mg) | KIM-1/ U Cr (ng/mg) |
|---|---|---|---|---|---|---|---|---|
| CHRONIC KIDNEY DISEASE | | | | | | | | |
| 1 | 73 | M | B | 15 | 4 | Diabetes, Hypertension | 3.98 | 1.24 |
| 2 | 62 | F | O | 19 | 4 | Chronic Interstitial Nephritis | 0.68 | 10.39 |
| 3 | 35 | F | W | 20 | 4 | Congenital Anomalies of the Kidney and Urinary Tract | 0.08 | 1.52 |
| 4 | 66 | F | W | 23 | 4 | Fibrillary Glomerulonephritis | 1.23 | 1.69 |
| 5 | 65 | F | W | 15 | 4 | Lithium Toxicity | 5.43 | 5.17 |
| 6 | 75 | F | B | 22 | 4 | Diabetes, Hypertension | 0.12 | 0.55 |
| 7 | 64 | M | W | 25 | 4 | Nephrectomy, recurrent Urinary Tract Infections | 2.75 | 0.80 |
| 8 | 56 | F | B | 20 | 4 | Hypertension | 3.74 | 0.95 |
| 9 | 64 | F | W | 13 | 5 | Diabetes and Phosphate Nephropathy | 2.05 | 3.55 |
| 10 | 39 | M | W | 6 | 5 | Chronic Interstitial Nephritis | 5.87 | 1.39 |
| 11 | 55 | M | B | 12 | 5 | Diabetes/Hypertension | 2.46 | 3.69 |
| 12 | 51 | M | W | 14 | 5 | Lupus | 1.68 | 7.42 |
| 13 | 74 | F | B | 13 | 5 | Nephrectomy, Hypertension | 2.85 | 2.15 |
| HEALTHY VOLUNTEERS | | | | | | | | |
| 14 | 21 | F | B | — | — | — | 0.28 | 0.43 |
| 15 | 27 | M | W | — | — | — | 0.92 | 0.19 |
| 16 | 21 | F | W | — | — | — | 1.93 | 0.90 |
| 17 | 21 | F | B | — | — | — | 0.92 | 0.57 |
| 18 | 29 | M | O | — | — | — | 1.38 | 1.34 |
| 19 | 19 | M | B | — | — | — | 0.28 | 0.28 |

TABLE 3-continued

Demographics and clinical characteristics of patients with or without chronic kidney disease (CKD).

| Participant | Age | Sex | Race | eGFR (ml/min/ 1.73 m$^2$) | Stage | Cause of CKD | SMOC2/ U Cr (ng/mg) | KIM-1/ U Cr (ng/mg) |
|---|---|---|---|---|---|---|---|---|
| 20 | 20 | M | O | — | — | — | 0.07 | 0.24 |
| 21 | 19 | M | W | — | — | — | 0.66 | 0.06 |
| 22 | 36 | F | W | — | — | — | 0.82 | 0.66 |
| 23 | 19 | M | O | — | — | — | 0.66 | 0.49 |
| 24 | 29 | F | O | — | — | — | 1.75 | 2.16 |
| 25 | 49 | F | B | — | — | — | 0.77 | 0.83 |
| 26 | 19 | F | O | — | — | — | 0.21 | 0.93 |

Example 2. SMOC2 Overexpressing Mice Exhibit Enhanced Kidney Fibrosis

Figure 2C:
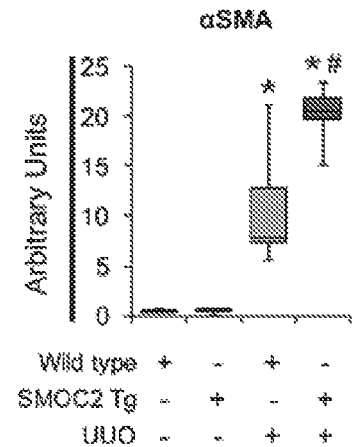
Figure 2D:
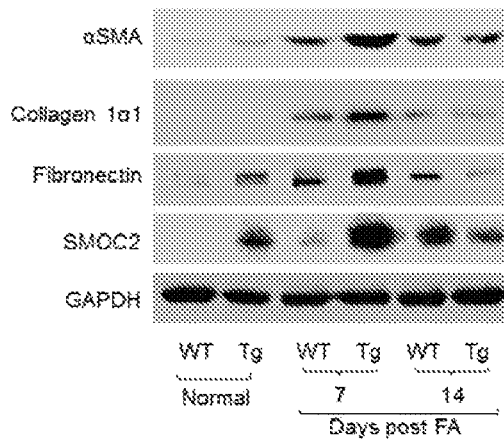
Figure 2E:
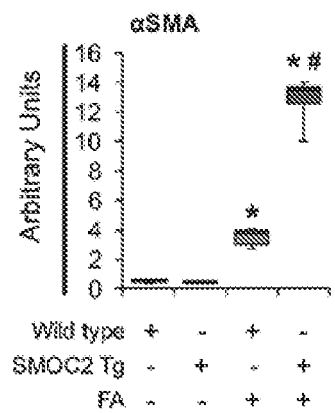
Figures 2F, 2G:
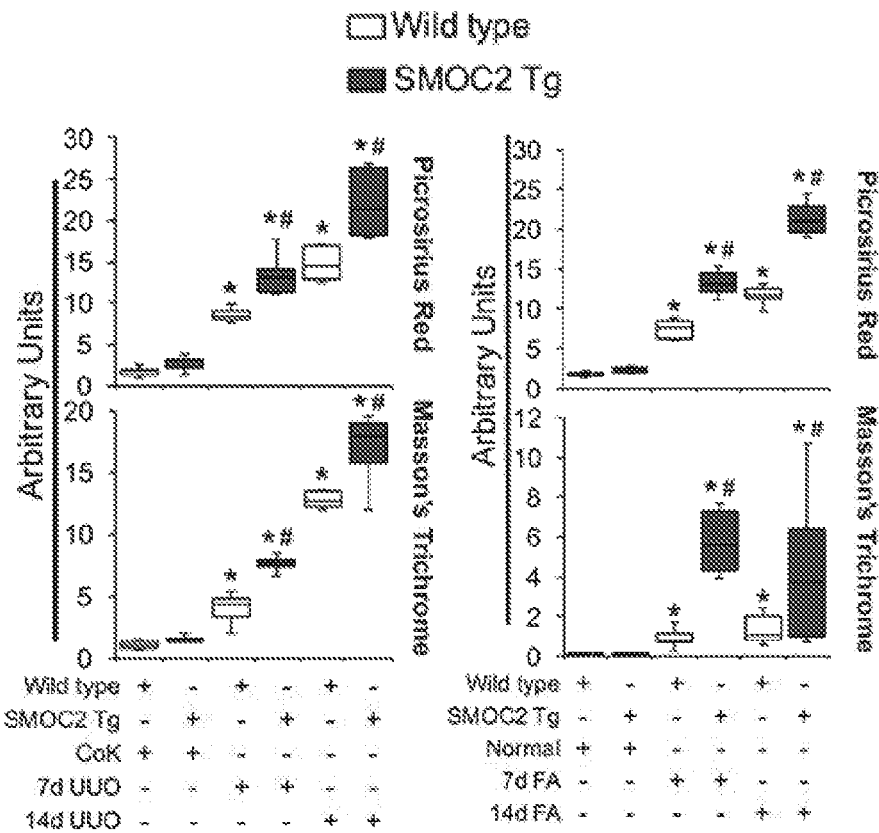

SMOC2 overexpressing transgenic mice (SMOC2 Tg) had markedly high SMOC2 levels (FIG. 2A) but normal histology of the heart, kidney, liver, lung, spleen, ovary, and testis. When subjected to UUO, SMOC2 Tg showed significantly greater fibrosis as compared to Wild type littermates as measured by mRNA (FIG. 10A) and protein levels (FIG. 2B, densitometry FIG. 10B) of αSMA, collagen and fibronectin in the kidneys at days 7 and 14 post-injury. This correlated with the ~2-fold greater presence of αSMA positive myofibroblasts in the interstitium (FIG. 2C). Similarly, SMOC2 Tg mice also demonstrated enhanced fibrosis when treated with FA (250 mg/kg ip) both at mRNA (FIG. 11A) and protein (FIG. 2D, densitometry FIG. 11B) levels. Moreover, αSMA positive myofibroblasts in the interstitium (FIG. 2E) were significantly elevated in the SMOC2 Tg mice as compared to Wild type mice following FA treatment. SMOC2 Tg mice also showed consistently higher amounts of pathological tubulointerstitial fibrosis than Wild type mice as detected by both Picrosirius Red and Masson's Trichrome staining of the kidneys at day 7 and 14 following UUO (FIG. 2F) or FA (FIG. 2G).

Example 3. SMOC2 Promotes Fibroblast to Myofibroblast Transition

Figure 3D:
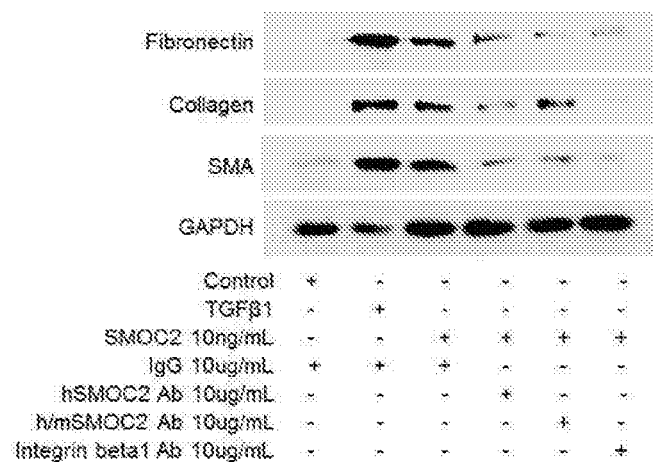
Figure 12A:
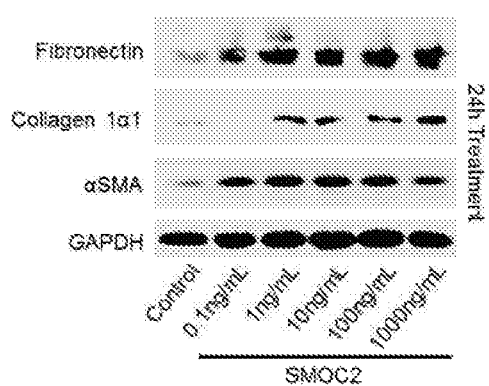
Figure 12B:
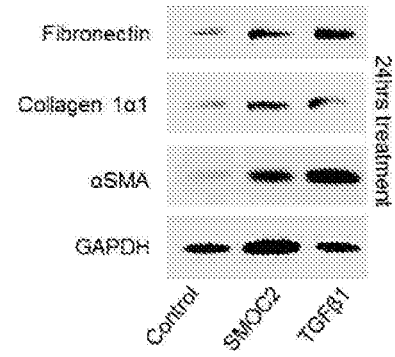
Figure 12C:
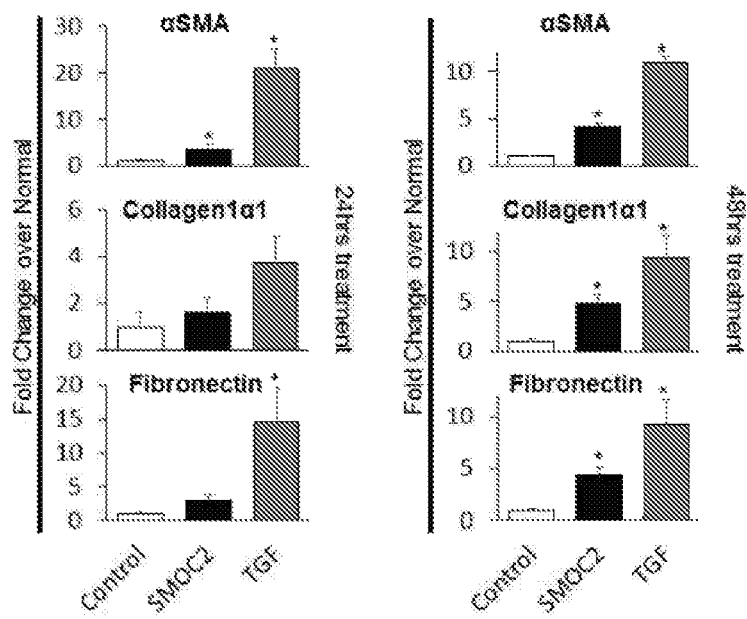
Figure 12D:
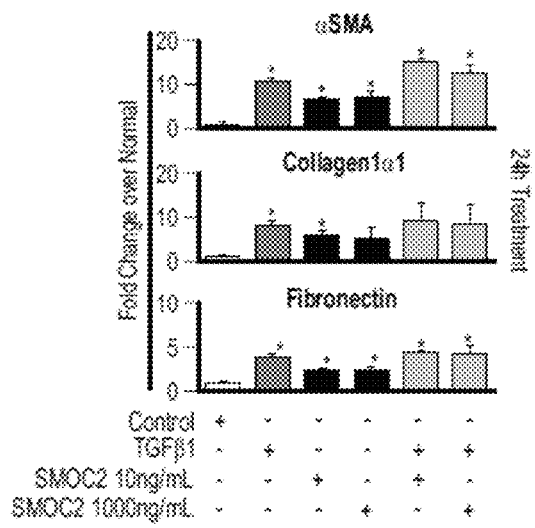
Figure 12E:
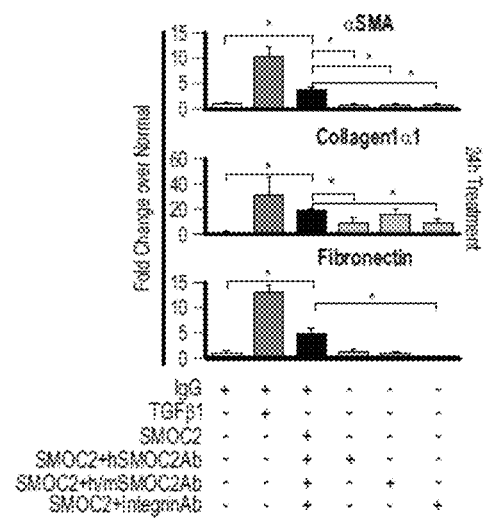
Figure 12F:
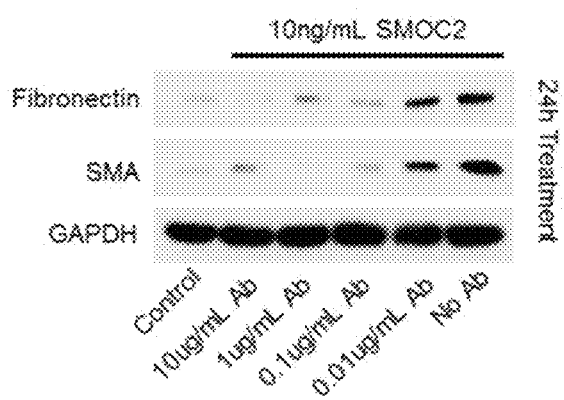
Figure 12G:
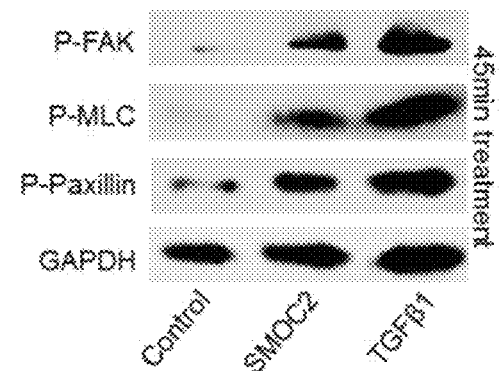

We performed RNA sequencing in SMOC2 Tg and Wild type mice kidneys at day 7 following UUO to investigate the mechanisms responsible for increased susceptibility of SMOC2 Tg mice to develop fibrosis. Gene set enrichment analysis (GSEA) for gene ontology (GO) and KEGG terms for cellular components revealed that genes in the ECM category represented a highly statistically significant difference between SMOC2 Tg and Wild type mice (FIG. 3A). Therefore, we investigated the potential of SMOC2 to transform fibroblasts (human primary kidney fibroblasts and NIH 3T3 fibroblasts) into myofibroblasts, which are the major cell type responsible for ECM production. In comparison to an induction of fibroblast to myofibroblast transition (FMT) by TGFβ1, SMOC2 (10 ng/mL, FIG. 12A) was also capable of inducing FMT as characterized by upregulation of αSMA, collagen 1α1 and fibronectin (FIGS. 3B, C and 12B-D). The specificity of SMOC2 to induce FMT was confirmed by preincubating SMOC2 with a SMOC2-specific antibody, which resulted in blocking the SMOC2 signaling effect on fibroblasts (FIG. 3D and FIG. 12E-F).

Figure 3E:
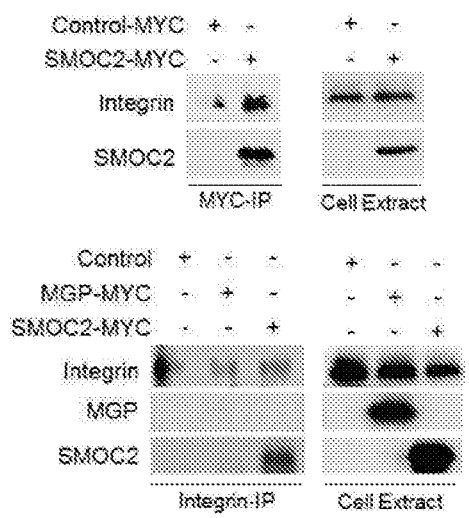

SMOC2 has been previously shown to bind keratinocytes through integrin β1 (Maier et al., Exp Cell Res. 2008 Aug. 1; 314(13):2477-87). To verify if the same applies to fibroblasts and might potentially be the mode of action for SMOC2, we first treated fibroblasts with an integrin β1 antibody prior to SMOC2 treatment. The integrin β1 antibody was effective in preventing the induction of FMT markers by SMOC2 (FIG. 3E). To confirm their interaction, we immunoprecipitated SMOC2 then blotted the pull-down for integrin β1, and vice versa. The results confirmed in a two-way analysis that SMOC2 also binds integrin β1 within the fibroblast cell type.

Figure 3F:
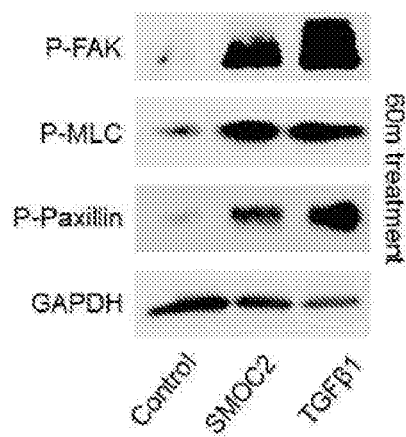
Figure 3G:
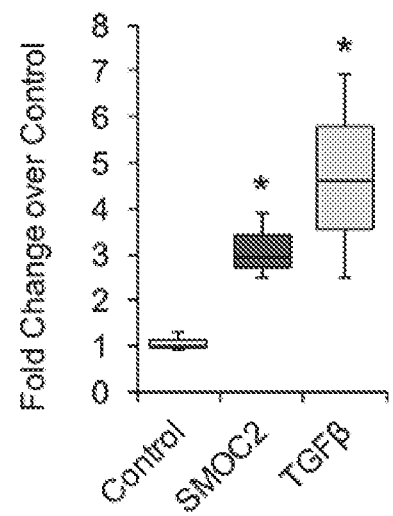
Figure 3H:
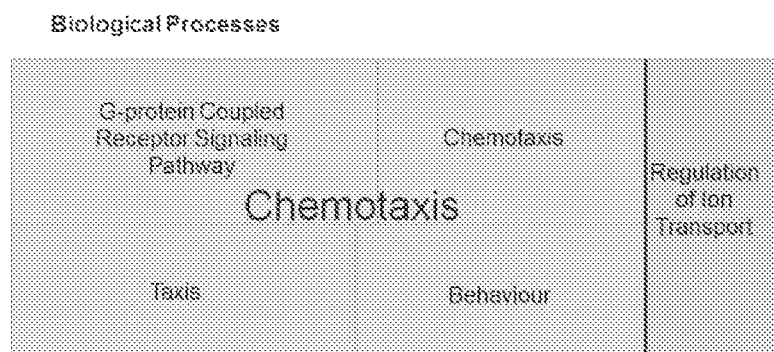
Figure 12H:
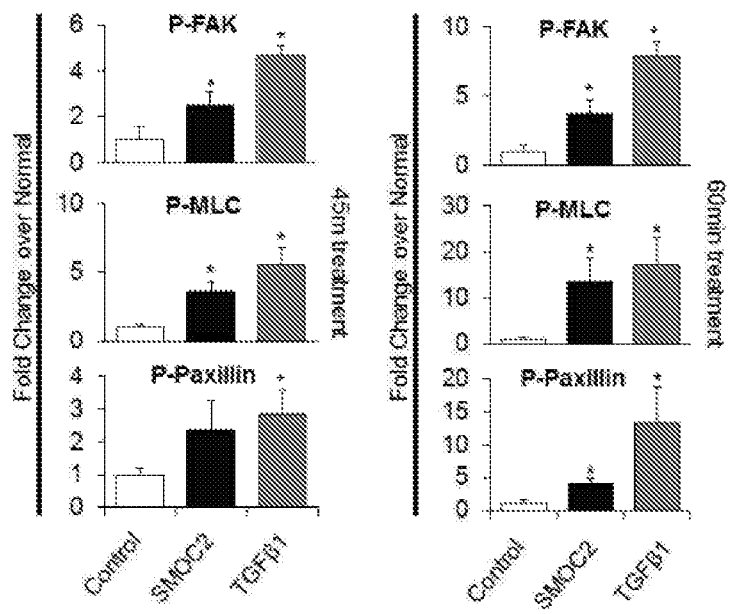
Figure 12I:
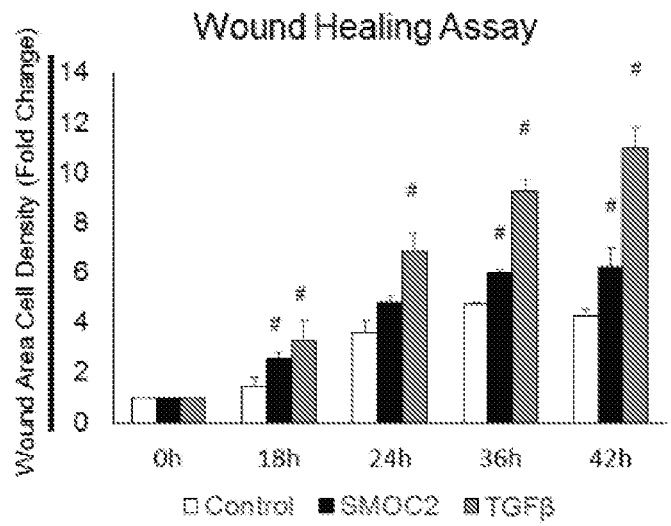
Figure 12J:
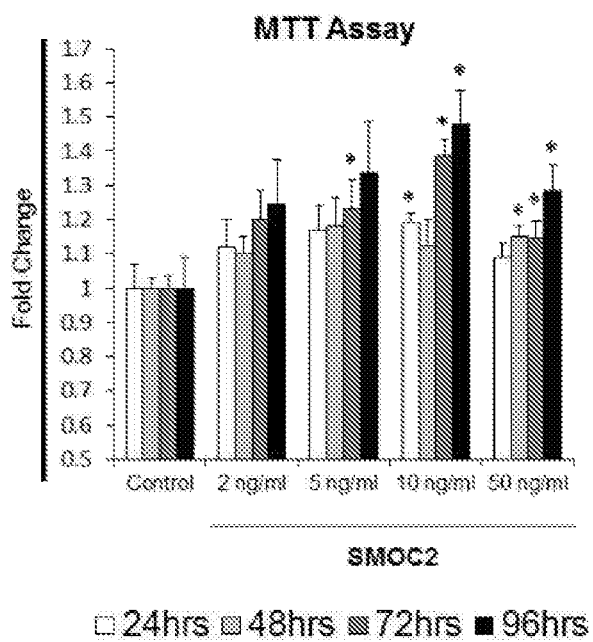
Figure 13A:
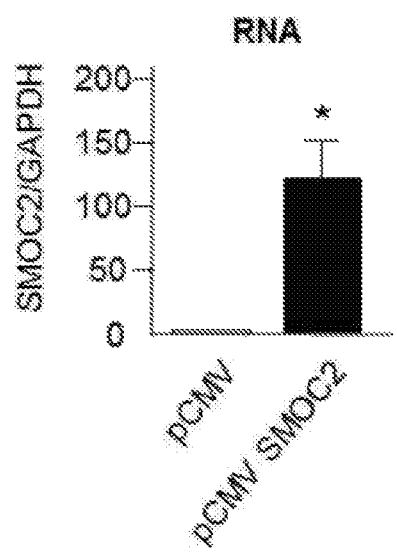
Figure 13B:
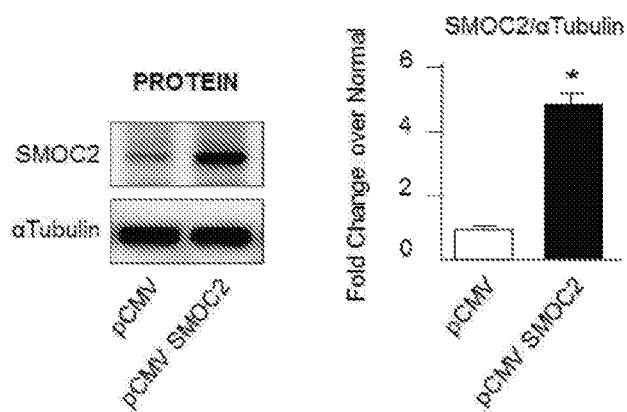
Figure 13C:
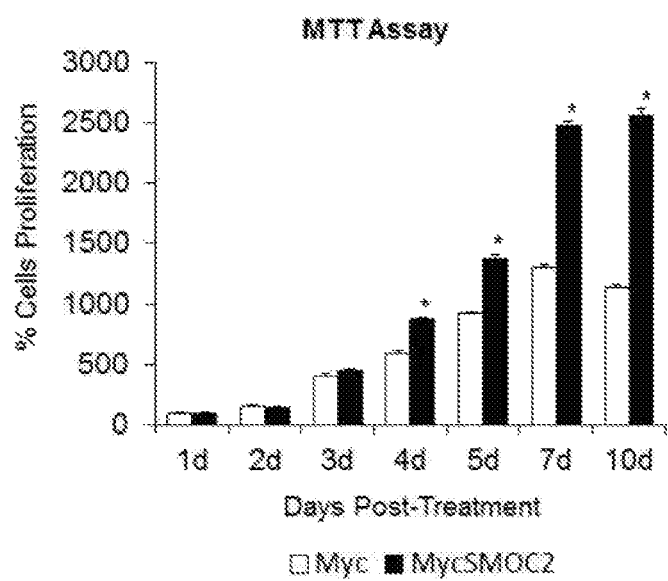
Figure 13D:
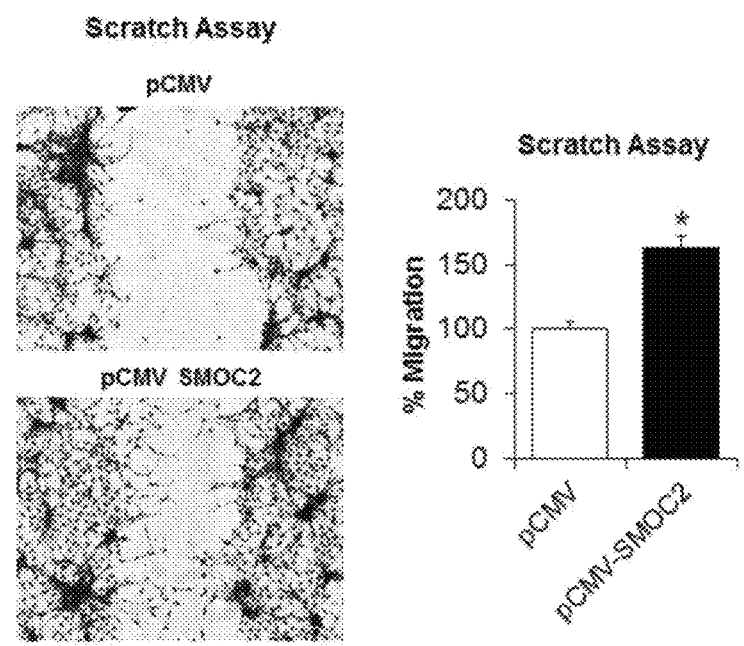
Figure 13E:
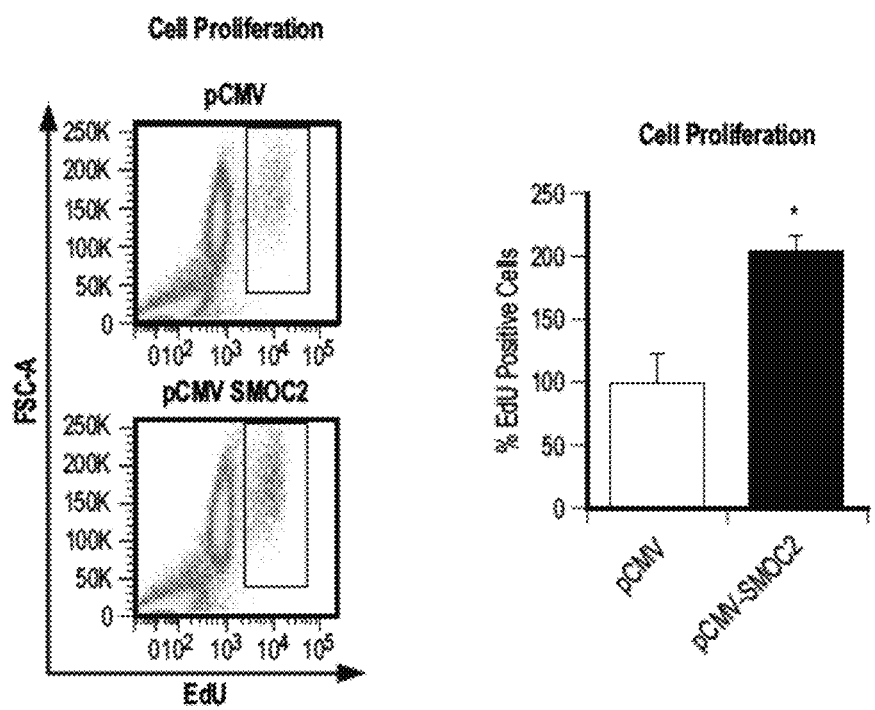
Figure 13F:
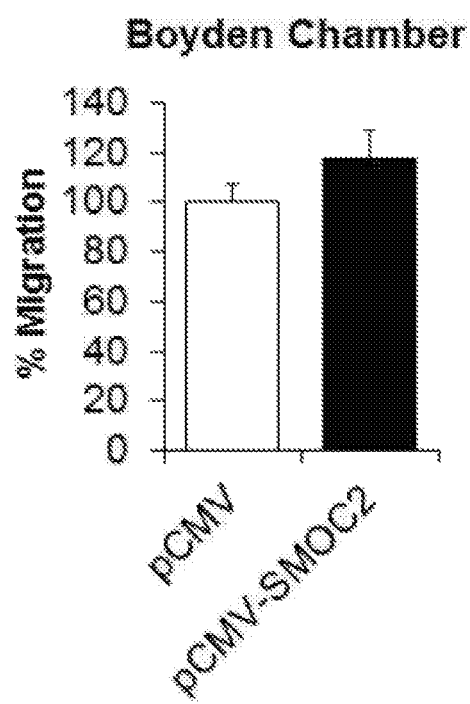
Figure 13G:
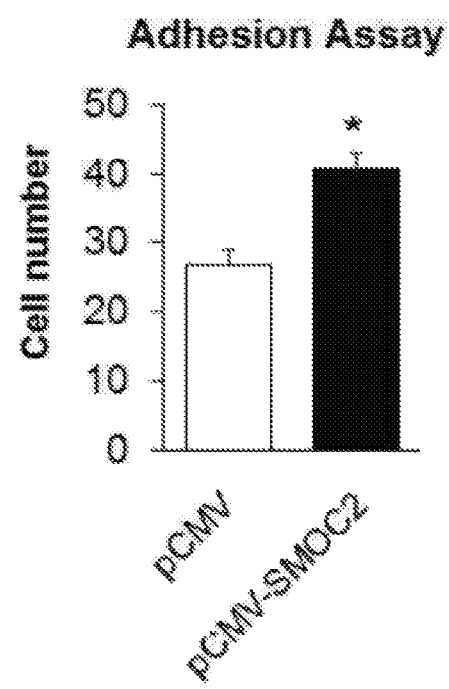

SMOC2 (10 ng/ml) treatment of quiescent fibroblasts also triggered an early cascade of integrin signaling events for FMT (14), including phosphorylation of focal adhesion kinase (FAK-P) (15, 16), myosin light chain (MLC-P) (17), and paxillin (Pax-P) (17), at 45 min (FIG. 12G-H) with a near double effect at 60 min (FIG. 3F, densitometry FIG. 12H). As αSMA expression culminates into the assembly of stress fiber, we next validated this structural formation after SMOC2 treatment of fibroblasts (FIG. 3G). Since RNA sequencing also revealed "Chemotaxis" as a highly significant biological process (FIG. 3H) between SMOC2 Tg and Wild type mice at 7 d following UUO, we investigated chemotactic properties of SMOC2 on fibroblasts by performing a scratch assay and Boyden Chamber-based migration assay. Fibroblasts treated with SMOC2 (10 ng/ml) for 24 h showed a significantly accelerated closure of the wound (FIG. 3I) created by a linear scrape on a monolayer of semi-confluent NIH3T3, which involved a significant repopulation of the wounded area over time (FIG. 12I). SMOC2 also enhanced migration of fibroblasts by ~50% (FIG. 12I). There was also ~3-fold increase in adhesion following SMOC2 treatment of fibroblasts (FIG. 3K). Furthermore, SMOC2 progressively increased the metabolic activity and survival of fibroblasts every 24 h over the course of 96 h (FIG. 3I, FIG. 12J). SMOC2 also showed mitogenic properties by stimulating fibroblast proliferation (p<0.05) as assessed by the number of EdU positive cells (FIG. 3M). In order to validate these effects of recombinant SMOC2 on fibroblasts, we also created SMOC2 overexpressing fibroblasts by transfecting NIH3T3 cells with pCMV-SMOC2 and observed similar phenotypic changes (FIGS. 13A-G). Taken together, these results suggest that SMOC2 stimulates fibroblast to myofibroblast (FMT) signaling with activation of its characteristic features including metabolic activity, proliferation, migration, and adhesion.

Example 4. SMOC2 Knockout Mice are Protected from Kidney Fibrosis

Figure 4C:
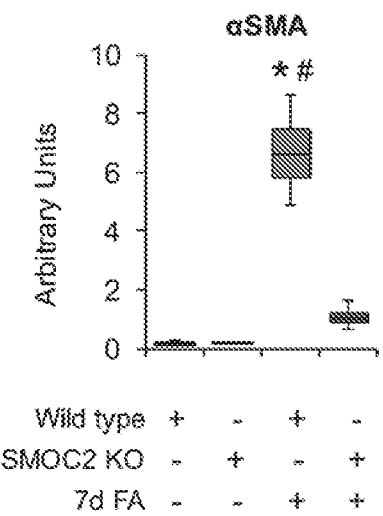
Figure 4D:
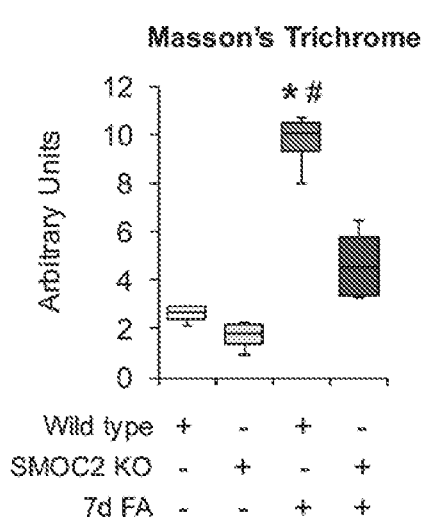
Figure 5A:
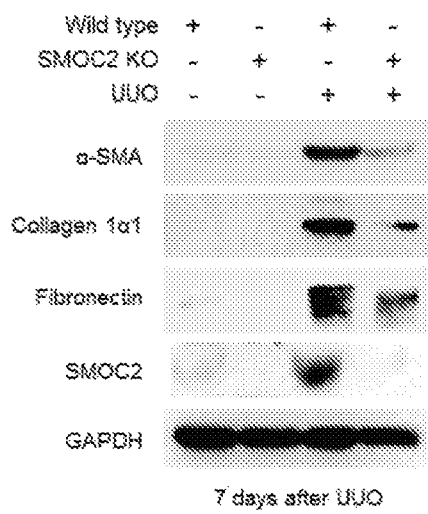
FIGS. 5A-C. Genetic inhibition of SMOC2 limits UUO-induced kidney fibrosis in mice. (A) Representative Western blot (n=5/group; densitometry in FIG. 15) of αSMA, collagen 1α1, fibronectin and SMOC2 expression using kidney samples obtained at day 7 from SMOC2 KO and Wild type (WT) mice subjected to UUO. (B) Images (n=3/group; 5 visual fields for each tissue analyzed) of immunofluorescent αSMA staining of KO and WT kidneys from normal mice and day 7 UUO mice. Relative quantitation is represented in a box plot as arbitrary units. (C) Masson's Trichrome staining of normal and 7 day UUO kidneys from WT and KO mice. Images of Masson's Trichrome staining are representative of 5-10 visual fields for each tissue analyzed. Quantification is represented in a box plot as arbitrary units (mice n=5-6, 5-10 visual fields/mice). Box plots describe the median (line within box), upper and lower quartiles (bounds of box), and minimum and maximum values (bars). *P<0.05 (WT CoK) and #P<0.05 (WT at respective UUO) determined by one-way analysis of variance (ANOVA) with Tukey post-hoc analysis.
Figure 5B:
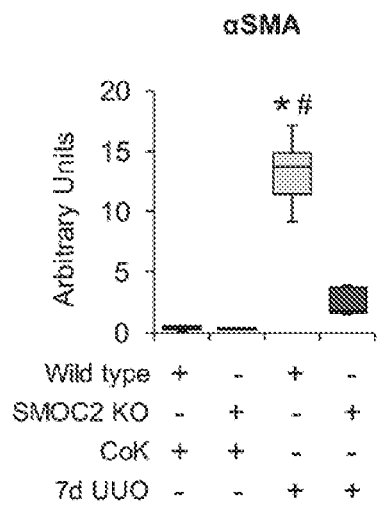
Figure 5C:
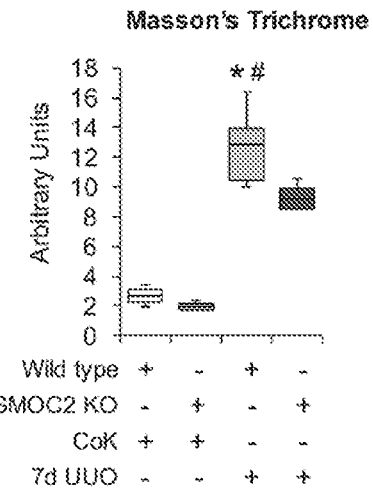

In order to investigate the effect of inhibition of SMOC2 on fibrosis progression, first, we used a genetic manipulation approach and confirmed that SMOC2 knockout (KO) mice (FIG. 4A) were histologically normal. When the SMOC2 KO mice were subjected to FA and UUO there was a marked attenuation of fibrotic markers at day 7 as compared to Wild type mice (FIG. 4B, densitometry FIG. 14; FIG. 5A, densitometry FIG. 18). This was confirmed by a significant decrease in αSMA positive cells in the interstitium (FIG. 4C and FIG. 5B), along with significant reduction in deposition and accumulation of ECM visualized by Masson's Trichrome staining (FIG. 4D).

Figure 6A:
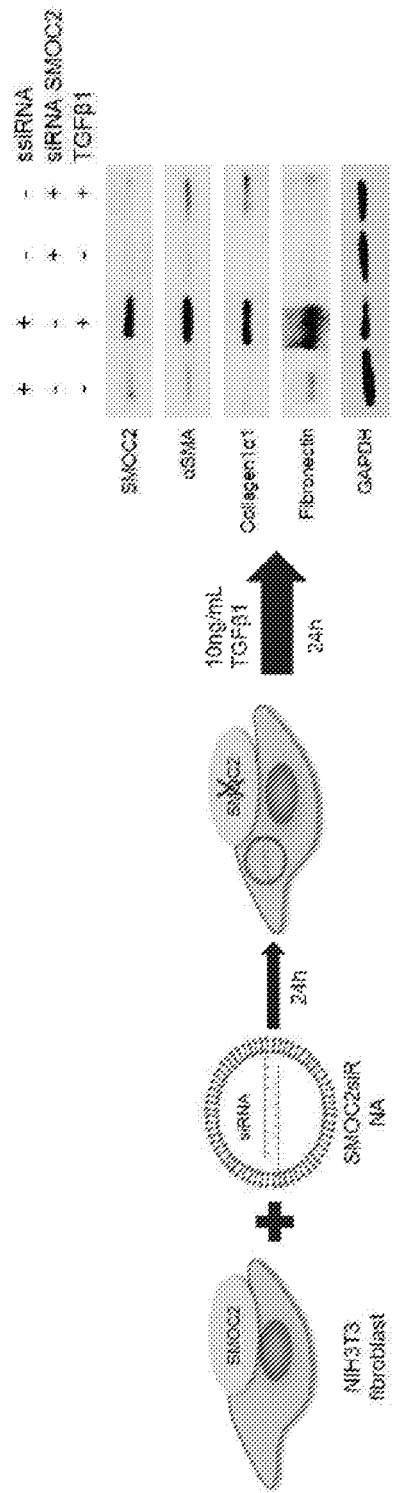
FIGS. 6A-D. Silencing SMOC2 reduces TGFβ1 induced fibrotic markers in vitro and folic acid-induced kidney fibrosis in mice. (A) Scheme of the experimental procedure for SMOC2 siRNA transfected NIH3T3 cells. After 24 h of treatment with SMOC2 siRNA or scrambled siRNA (ssiRNA), NIH3T3 fibroblasts were either treated with/out TGFβ1 for 24 h. Representative Western blot (n=3/condition; densitometry in FIG. 17) was performed for SMOC2, αSMA, collagen 1α1 and fibronectin expression. (B)
Figure 6B:
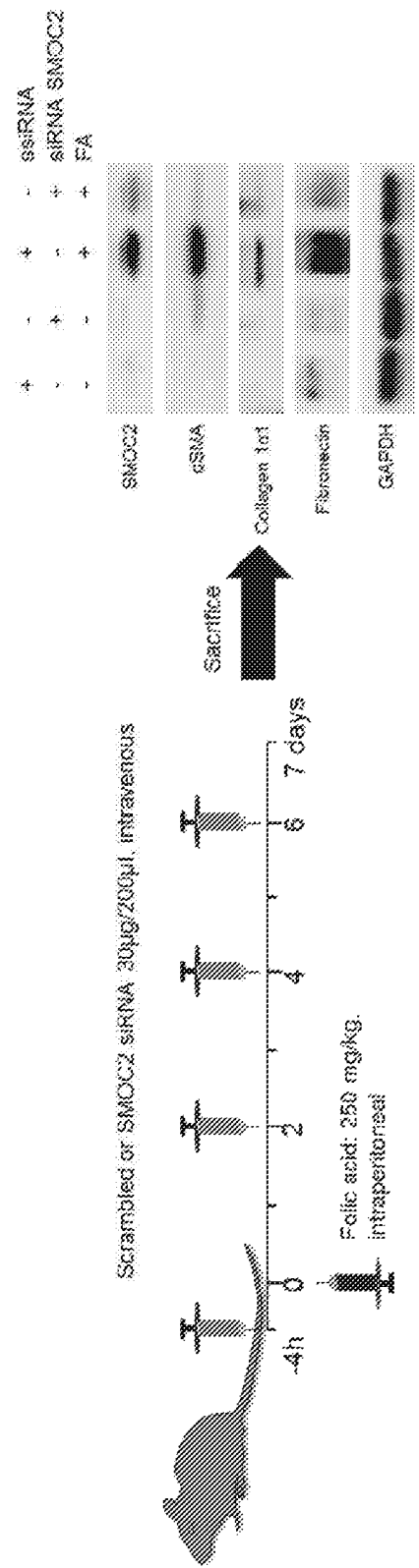
Figure 6C:
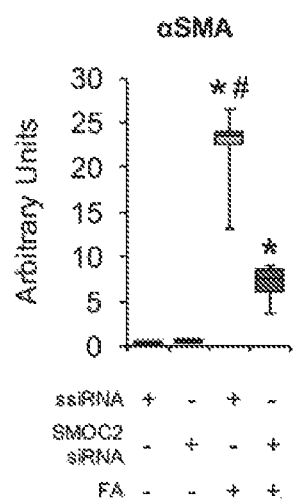
Figure 6D:
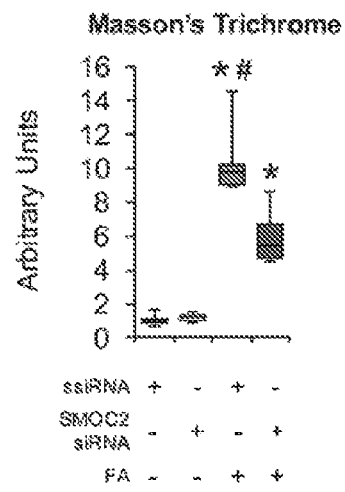

Example 5. Targeting SMOC2 Using RNA Interference Protects Against Fibrosis Development Next, we used a pharmacological inhibition approach to inhibit SMOC2 by synthesizing small interfering RNAs (siRNAs). We tested the efficacy of 4 siRNAs and found one (target sequence: UCUGAACUCUGAAUUUAA; SEQ ID NO:17; SMOC2 siRNA used in mouse studies: Sense (5' to 3'): UUC UGA ACU CUG AAU UUA AUU (SEQ ID NO:18); Antisense (5' to 3'): UUA AAU UCA GAG UUC AGA AUU (SEQ ID NO:19)) that resulted in ~90% silencing in vitro (SMOC2 siRNA #16 in FIG. 16); the same sequences could be used to target human SMOC2 due to the high level of homology between human and murine sequences. NIH3T3 cells transfected with SMOC2 siRNA resulted in significant attenuation of TGFβ1-mediated fibroblast to myofibroblast transition and signaling as measured by a significant decrease in SMOC2, αSMA, collagen 1α1 and fibronectin expression (FIG. 6A, densitometry FIG. 17). Using the same SMOC2 siRNA sequence we then synthesized endotoxin free, chemically modified SMOC2 siRNA that is resistant to degradation in vivo and localizes in the kidneys (18) (FIG. 18). SMOC2 siRNA when injected into mice intravenously also resulted in ~50% reduction in kidney SMOC2 protein expression following FA administration (FIG. 6B, densitometry FIG. 19) thereby establishing proof of delivery. More importantly, a significant amelioration of kidney fibrosis was observed in mice treated with SMOC2 siRNA as compared to scrambled siRNA (ssiRNA) at day 7 following FA treatment (FIG. 6Bs, densitometry FIG. 19). Myofibroblast transformation and collagen accumulation as assessed by αSMA staining and Masson's Trichrome staining, respectively, was significantly less in FA-injected mice treated with SMOC2 siRNA (FIGS. 6c and 6d) compared to ssiRNA treated mice.

REFERENCES

1. Nanthakumar C B, Hatley R J, Lemma S, Gauldie J, Marshall R P, and Macdonald S J. Dissecting fibrosis: therapeutic insights from the small-molecule toolbox. Nat Rev Drug Discov. 2015; 14 (10):693-720.
2. Ferenbach D A, and Bonventre J V. Mechanisms of maladaptive repair after A M leading to accelerated kidney ageing and CKD. Nat Rev Nephrol. 2015; 11 (5): 264-76.
3. Breyer M D, and Susztak K. The next generation of therapeutics for chronic kidney disease. Nat Rev Drug Discov. 2016.
4. Grgic I, Duffield J S, and Humphreys B D. The origin of interstitial myofibroblasts in chronic kidney disease. Pediatr Nephrol. 2012; 27 (2):183-93.
5. Duffield J S. Cellular and molecular mechanisms in kidney fibrosis. J Clin Invest. 2014; 124 (6):2299-306.
6. Tomasek J J, Gabbiani G, Hinz B, Chaponnier C, and Brown R A. Myofibroblasts and mechano-regulation of connective tissue remodelling. Nat Rev Mol Cell Biol. 2002; 3 (5):349-63.
7. Hinz B. It has to be the alphav: myofibroblast integrins activate latent TGF-beta1. Nat Med. 2013; 19 (12):1567-8.
8. Meran S, and Steadman R. Fibroblasts and myofibroblasts in renal fibrosis. Int J Exp Pathol. 2011; 92 (3):158-67.
9. LeBleu V S, Taduri G, O'Connell J, Teng Y, Cooke V G, Woda C, Sugimoto H, and Kalluri R. Origin and function of myofibroblasts in kidney fibrosis. Nat Med. 2013; 19 (8):1047-53.
10. Craciun F L, Bijol V, Ajay A K, Rao P, Kumar R K, Hutchinson J, Hofmann O, Joshi N, Luyendyk J P, Kusebauch U, et al. RNA Sequencing Identifies Novel Translational Biomarkers of Kidney Fibrosis. J Am Soc Nephrol. 2016; 27 (6):1702-13. Epub 2015 Oct. 8.
11. Wong G S, and Rustgi A K. Matricellular proteins: priming the tumour microenvironment for cancer development and metastasis. Br J Cancer. 2013; 108 (4):755-61.
12. Schellings M W, Pinto Y M, and Heymans S. Matricellular proteins in the heart: possible role during stress and remodeling. Cardiovasc Res. 2004; 64 (1):24-31.
13. Jendraschak E, and Sage E H. Regulation of angiogenesis by SPARC and angiostatin: implications for tumor cell biology. Semin Cancer Biol. 1996; 7 (3):139-46.
14. Mitra S K, Hanson D A, and Schlaepfer D D. Focal adhesion kinase: in command and control of cell motility. Nat Rev Mol Cell Biol. 2005; 6 (1):56-68.
15. Mimura Y, Ihn H, Jinnin M, Asano Y, Yamane K, and Tamaki K. Constitutive phosphorylation of focal adhesion kinase is involved in the myofibroblast differentiation of scleroderma fibroblasts. J Invest Dermatol. 2005; 124 (5):886-92.
16. Greenberg R S, Bernstein A M, Benezra M, Gelman I H, Taliana L, and Masur S K. FAK-dependent regulation of myofibroblast differentiation. FASEB J. 2006; 20 (7): 1006-8.
17. Gerarduzzi C, He Q, Antoniou J, and Di Battista J A. Prostaglandin E (2)-dependent blockade of actomyosin and stress fibre formation is mediated through S1379 phosphorylation of ROCK2. J Cell Biochem. 2014; 115 (9):1516-27.
18. Chau B N, Xin C, Hartner J, Ren S, Castano A P, Linn G, Li J, Tran P T, Kaimal V, Huang X, et al. MicroRNA-21 promotes fibrosis of the kidney by silencing metabolic pathways. Sci Transl Med. 2012; 4 (121):121ra18.
19. Humphrey J D, Dufresne E R, and Schwartz M A. Mechanotransduction and extracellular matrix homeostasis. Nat Rev Mol Cell Biol. 2014; 15 (12):802-12.
20. McCurdy S, Baicu C F, Heymans S, and Bradshaw A D. Cardiac extracellular matrix remodeling: fibrillar collagens and Secreted Protein Acidic and Rich in Cysteine (SPARC). J Mol Cell Cardiol. 2010; 48 (3):544-9.
21. Sasaki T, Hohenester E, Gohring W, and Timpl R. Crystal structure and mapping by site-directed mutagenesis of the collagen-binding epitope of an activated form of BM-40/SPARC/osteonectin. EMBO J. 1998; 17 (6): 1625-34.
22. Bradshaw A D, Baicu C F, Rentz T J, Van Laer A O, Boggs J, Lacy J M, and Zile M R. Pressure overload-induced alterations in fibrillar collagen content and myocardial diastolic function: role of secreted protein acidic and rich in cysteine (SPARC) in post-synthetic procollagen processing. Circulation. 2009; 119 (2):269-80.
23. Maier S, Paulsson M, and Hartmann U. The widely expressed extracellular matrix protein SMOC-2 promotes keratinocyte attachment and migration. Exp Cell Res. 2008; 314 (13):2477-87.

24. Pazin D E, and Albrecht K H. Developmental expression of Smoc1 and Smoc2 suggests potential roles in fetal gonad and reproductive tract differentiation. Dev Dyn. 2009; 238 (11):2877-90.
25. Rocnik E F, Liu P, Sato K, Walsh K, and Vaziri C. The novel SPARC family member SMOC-2 potentiates angiogenic growth factor activity. J Biol Chem. 2006; 281 (32):22855-64.
26. Liu P, Lu J, Cardoso W V, and Vaziri C. The SPARC-related factor SMOC-2 promotes growth factor-induced cyclin D1 expression and DNA synthesis via integrin-linked kinase. Mol Biol Cell. 2008; 19 (1):248-61.
27. Bornstein P, and Sage E H. Matricellular proteins: extracellular modulators of cell function. Curr Opin Cell Biol. 2002; 14 (5):608-16.
28. Grinnell F. Fibroblast biology in three-dimensional collagen matrices. Trends Cell Biol. 2003; 13 (5):264-9.
29. Craciun F L, Ajay A K, Hoffmann D, Saikumar J, Fabian S L, Bijol V, Humphreys B D, and Vaidya V S. Pharmacological and genetic depletion of fibrinogen protects from kidney fibrosis. Am J Physiol Renal Physiol. 2014; 307 (4):F471-84.
30. Martin M. Cutadapt removes adapter sequences from high-throughput sequencing reads. 2011. 2011; 17 (1).
31. Dobin A, Davis C A, Schlesinger F, Drenkow J, Zaleski C, Jha S, Batut P, Chaisson M, and Gingeras T R. STAR: ultrafast universal RNA-seq aligner. Bioinformatics. 2013; 29 (1):15-21.
32. Garcia-Alcalde F, Okonechnikov K, Carbonell J, Cruz L M, Gotz S, Tarazona S, Dopazo J, Meyer T F, and Conesa A. Qualimap: evaluating next-generation sequencing alignment data. Bioinformatics. 2012; 28 (20):2678-9.
33. Liao Y, Smyth G K, and Shi W. featureCounts: an efficient general purpose program for assigning sequence reads to genomic features. Bioinformatics. 2014; 30 (7): 923-30.
34. Love M I, Huber W, and Anders S. Moderated estimation of fold change and dispersion for RNA-seq data with DESeq2. Genome Biol. 2014; 15 (12):550.
35. Luo W, Friedman M S, Shedden K, Hankenson K D, and Woolf P J. GAGE: generally applicable gene set enrichment for pathway analysis. BMC Bioinformatics. 2009; 10 (161.
36. Supek F, Bosnjak M, Skunca N, and Smuc T. REVIGO summarizes and visualizes long lists of gene ontology terms. PLoS One. 2011; 6 (7):e21800.
37. Masur S K, Dewal H S, Dinh T T, Erenburg I, and Petridou S. Myofibroblasts differentiate from fibroblasts when plated at low density. Proc Natl Acad Sci USA. 1996; 93 (9):4219-23.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for prophylaxis of kidney fibrosis in a subject who is at risk of developing kidney fibrosis, the method comprising administering to the subject a therapeutically effective amount of an inhibitor of Secreted Modular Calcium-binding protein 2 (SMOC2), wherein the inhibitor is a monoclonal antibody or antigen binding portion thereof that binds specifically to SMOC2, and wherein the administration results in prophylaxis of kidney fibrosis in the subject.

2. The method of claim 1, wherein the monoclonal antibody or antigen binding portion thereof is chimeric, humanized, or fully human.

3. A method for prophylaxis of kidney fibrosis in a subject who is at risk of developing kidney fibrosis, the method comprising administering to the subject a therapeutically effective amount of an inhibitor of Secreted Modular Calcium-binding protein 2 (SMOC2), wherein the inhibitor is an inhibitory nucleic acid that targets a SMOC2 transcript, and wherein the administration results in prophylaxis of kidney fibrosis in the subject.

4. The method of claim 3, wherein the inhibitory nucleic acid is selected from the group consisting of antisense oligonucleotides, small interfering RNAs (siRNAs), small hairpin RNAs (shRNAs).

5. The method of claim 4, wherein the inhibitory nucleic acid is modified.

6. The method of claim 5, wherein the inhibitory nucleic acid comprises a modified backbone.

7. The method of claim 6, wherein the backbone is an amide or morpholino backbone.

8. The method of claim 5, wherein the inhibitory nucleic acid comprises one or more modified nucleosides.

9. The method of claim 8, comprising at least one locked nucleoside.

10. The method of claim 1, wherein the subject has a condition associated with kidney fibrosis selected from chronic kidney disease, vesicoureteral reflux, tubulointerstitial renal fibrosis, diabetes, and glomerular nephritis (GN).

11. The method of claim 10, wherein the GN is focal segmental glomerulosclerosis and membranous glomerulonephritis or mesangiocapillary GN.

12. The method of claim 1, wherein the subject is at risk of developing kidney fibrosis resulting from metabolic syndrome or diabetes.

13. The method of claim 3, wherein the subject has a condition associated with kidney fibrosis selected from chronic kidney disease, vesicoureteral reflux, tubulointerstitial renal fibrosis, diabetes, and glomerular nephritis (GN).

14. The method of claim 13, wherein the GN is focal segmental glomerulosclerosis and membranous glomerulonephritis or mesangiocapillary GN.

15. The method of claim 3, wherein the subject is at risk of developing kidney fibrosis resulting from metabolic syndrome or diabetes.

* * * * *

SEQUENCE LISTING

<160> NUMBER OF SEQ ID NOS: 19

<210> SEQ ID NO 1
<211> LENGTH: 20
<212> TYPE: DNA
<213> ORGANISM: Artificial Sequence
<220> FEATURE:
<223> OTHER INFORMATION: Wild type F primer

<400> SEQUENCE: 1
tccttctcca gcaccaagtc                                              20

<210> SEQ ID NO 2
<211> LENGTH: 20
<212> TYPE: DNA
<213> ORGANISM: Artificial Sequence
<220> FEATURE:
<223> OTHER INFORMATION: Wild type R primer

<400> SEQUENCE: 2
tgatccaaaa gtgcctcctc                                              20

<210> SEQ ID NO 3
<211> LENGTH: 20
<212> TYPE: DNA
<213> ORGANISM: Artificial Sequence
<220> FEATURE:
<223> OTHER INFORMATION: KO F primer

<400> SEQUENCE: 3
cggtcgctac cattaccagt                                              20

<210> SEQ ID NO 4
<211> LENGTH: 24

```
<212> TYPE: DNA
<213> ORGANISM: Artificial Sequence
<220> FEATURE:
<223> OTHER INFORMATION: KO R primer

<400> SEQUENCE: 4
catgctctga gaaataatta ccaa                                              24

<210> SEQ ID NO 5
<211> LENGTH: 20
<212> TYPE: DNA
<213> ORGANISM: Artificial Sequence
<220> FEATURE:
<223> OTHER INFORMATION: Transgenic F primer

<400> SEQUENCE: 5
tgacagcagc agcggcagtt                                                   20

<210> SEQ ID NO 6
<211> LENGTH: 19
<212> TYPE: DNA
<213> ORGANISM: Artificial Sequence
<220> FEATURE:
<223> OTHER INFORMATION: Transgenic R primer

<400> SEQUENCE: 6
tagcggctga agcactgca                                                    19

<210> SEQ ID NO 7
<211> LENGTH: 21
<212> TYPE: DNA
<213> ORGANISM: Artificial Sequence
<220> FEATURE:
<223> OTHER INFORMATION: aSMA F primer

<400> SEQUENCE: 7
gtcccagaca tcagggagta a                                                 21

<210> SEQ ID NO 8
<211> LENGTH: 21
<212> TYPE: DNA
<213> ORGANISM: Artificial Sequence
<220> FEATURE:
<223> OTHER INFORMATION: aSMA R primer

<400> SEQUENCE: 8
tcggatactt cagcgtcagg a                                                 21

<210> SEQ ID NO 9
<211> LENGTH: 21
<212> TYPE: DNA
<213> ORGANISM: Artificial Sequence
<220> FEATURE:
<223> OTHER INFORMATION: Fibronectin F primer

<400> SEQUENCE: 9
atgtggaccc ctcctgatag t                                                 21

<210> SEQ ID NO 10
<211> LENGTH: 21
<212> TYPE: DNA
<213> ORGANISM: Artificial Sequence
<220> FEATURE:
<223> OTHER INFORMATION: Fibronectin R primer

<400> SEQUENCE: 10
```
gcccagtgat tcagcaaag g                                                   21

<210> SEQ ID NO 11
<211> LENGTH: 20
<212> TYPE: DNA
<213> ORGANISM: Artificial Sequence
<220> FEATURE:
<223> OTHER INFORMATION: Smoc2 F primer

<400> SEQUENCE: 11
ccgtacaaga actgatgggc                                                    20

<210> SEQ ID NO 12
<211> LENGTH: 20
<212> TYPE: DNA
<213> ORGANISM: Artificial Sequence
<220> FEATURE:
<223> OTHER INFORMATION: Smoc2 R primer

<400> SEQUENCE: 12
ctttcagcat gacctctggg                                                    20

<210> SEQ ID NO 13
<211> LENGTH: 20
<212> TYPE: DNA
<213> ORGANISM: Artificial Sequence
<220> FEATURE:
<223> OTHER INFORMATION: Col1a1 F primer

<400> SEQUENCE: 13
tgactggaag agcggagagt                                                    20

<210> SEQ ID NO 14
<211> LENGTH: 20
<212> TYPE: DNA
<213> ORGANISM: Artificial Sequence
<220> FEATURE:
<223> OTHER INFORMATION: Col1a1 R primer

<400> SEQUENCE: 14
gttcgggctg atgtaccagt                                                    20

<210> SEQ ID NO 15
<211> LENGTH: 22
<212> TYPE: DNA
<213> ORGANISM: Artificial Sequence
<220> FEATURE:
<223> OTHER INFORMATION: GAPDH F primer

<400> SEQUENCE: 15
attgccctca acgaccactt tg                                                 22

<210> SEQ ID NO 16
<211> LENGTH: 24
<212> TYPE: DNA
<213> ORGANISM: Artificial Sequence
<220> FEATURE:
<223> OTHER INFORMATION: GADPH R primer

<400> SEQUENCE: 16
tctctcttcc tcttgtgctc ttgc                                               24

<210> SEQ ID NO 17
<211> LENGTH: 18
<212> TYPE: RNA
<213> ORGANISM: Artificial Sequence

```
<220> FEATURE:
<223> OTHER INFORMATION: siRNA target sequence

<400> SEQUENCE: 17
ucugaacucu gaauuuaa                                                    18

<210> SEQ ID NO 18
<211> LENGTH: 21
<212> TYPE: RNA
<213> ORGANISM: Artificial Sequence
<220> FEATURE:
<223> OTHER INFORMATION: SMOC2 siRNA Sense

<400> SEQUENCE: 18
uucugaacuc ugaauuuaau u                                                21

<210> SEQ ID NO 19
<211> LENGTH: 21
<212> TYPE: RNA
<213> ORGANISM: Artificial Sequence
<220> FEATURE:
<223> OTHER INFORMATION: SMOC2 siRNA Antisense

<400> SEQUENCE: 19
uuaaauucag aguucagaau u                                                21
```